US012629059B2

(12) United States Patent
Dowd et al.

(10) Patent No.: US 12,629,059 B2
(45) Date of Patent: May 19, 2026

(54) GLUCOSE LEVEL DEVIATION DETECTION

(71) Applicant: Dexcom, Inc., San Diego, CA (US)

(72) Inventors: Robert J. Dowd, San Diego, CA (US); Margaret A. Crawford, San Diego, CA (US); Mark Derdzinski, San Diego, CA (US); Lauren H. Jepson, San Diego, CA (US); Giada Acciaroli, San Diego, CA (US); Sarah Kate Pickus, San Diego, CA (US); Apurv U. Kamath, San Diego, CA (US)

(73) Assignee: DEXCOM, INC., San Diego, CA (US)

( * ) Notice: Subject to any disclaimer, the term of this patent is extended or adjusted under 35 U.S.C. 154(b) by 674 days.

(21) Appl. No.: 17/974,190

(22) Filed: Oct. 26, 2022

(65) Prior Publication Data

US 2023/0134919 A1 May 4, 2023

Related U.S. Application Data

(60) Provisional application No. 63/292,942, filed on Dec. 22, 2021, provisional application No. 63/263,188, filed on Oct. 28, 2021.

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/7267* (2013.01); *A61B 5/7275* (2013.01);
(Continued)

(58) Field of Classification Search
CPC . A61B 5/14532; A61B 5/7267; A61B 5/7275; A61B 5/742; G16H 50/30;
(Continued)

(56) References Cited

U.S. PATENT DOCUMENTS

| | | | |
|---|---|---|---|
| 2003/0208113 A1 | 11/2003 | Mault et al. | |
| 2009/0055149 A1 | 2/2009 | Hayter et al. | |

(Continued)

FOREIGN PATENT DOCUMENTS

| | | |
|---|---|---|
| WO | 2010022387 A1 | 2/2010 |
| WO | 2020139771 A1 | 7/2020 |

OTHER PUBLICATIONS

Dadlani V., et al., "High Glucose Variability in Hospitalized Patients with Type 1 Diabetes Mellitus," Diabetes Technology & Therapeutics, vol. 19, No. 10, 2017, pp. 572-579.

(Continued)

*Primary Examiner* — Eric F Winakur
*Assistant Examiner* — Hy Khanh Doan
(74) *Attorney, Agent, or Firm* — Patterson + Sheridan, LLP

(57) ABSTRACT

Glucose level measurements of a user are obtained over time, such as from a wearable glucose monitoring device being worn by the user. These glucose level measurements can be produced substantially continuously, such that the device may be configured to produce the glucose level measurements at regular or irregular intervals of time, responsive to establishing a communicative coupling with a different device, and so forth. These glucose level measurements are analyzed to detect deviations from past glucose measurements, such as glucose measurements received earlier in the day or glucose measurements received at corresponding times of one or more preceding days. Indications of detected deviations are provided to the user or communicated elsewhere, such as to a healthcare professional.

19 Claims, 8 Drawing Sheets

(51) Int. Cl.
*G16H 50/30* (2018.01)
*G16H 50/70* (2018.01)

(52) U.S. Cl.
CPC ............ *A61B 5/742* (2013.01); *G16H 50/30* (2018.01); *G16H 50/70* (2018.01)

(58) Field of Classification Search
CPC ........ G16H 50/70; G16H 20/30; G16H 20/60; G16H 20/17; G16H 40/63
See application file for complete search history.

(56) References Cited

U.S. PATENT DOCUMENTS

| | | | |
|---|---|---|---|
| 2010/0095229 | A1 | 4/2010 | Dixon et al. |
| 2010/0257214 | A1 | 10/2010 | Bessette |
| 2015/0120317 | A1 | 4/2015 | Mayou et al. |
| 2015/0289823 | A1 | 10/2015 | Rack-Gomer et al. |
| 2016/0098848 | A1 | 4/2016 | Zamanakos et al. |
| 2017/0049386 | A1 | 2/2017 | Abraham et al. |
| 2017/0181645 | A1 | 6/2017 | Mahalingam et al. |
| 2017/0311903 | A1 | 11/2017 | Davis et al. |
| 2018/0001184 | A1 | 1/2018 | Tran et al. |
| 2018/0137938 | A1 | 5/2018 | Vaddiraju et al. |
| 2018/0169437 | A1 | 6/2018 | Carpenter et al. |
| 2018/0286507 | A1 | 10/2018 | Gass et al. |
| 2018/0326150 | A1 | 11/2018 | Davis et al. |
| 2019/0381243 | A1 | 12/2019 | Bowland et al. |
| 2019/0385721 | A1 | 12/2019 | Bowland et al. |
| 2020/0051699 | A1 | 2/2020 | Tahmasebi Maraghoosh |
| 2020/0203012 | A1 | 6/2020 | Kamath et al. |
| 2021/0193328 | A1 | 6/2021 | Patek |
| 2021/0205535 | A1 | 7/2021 | Lee et al. |
| 2021/0290111 | A1 | 9/2021 | Liu et al. |
| 2022/0020499 | A1 | 1/2022 | Schuster et al. |
| 2023/0329650 | A1 | 10/2023 | Bhattacharya et al. |
| 2024/0127911 | A1 | 4/2024 | Uchida et al. |

OTHER PUBLICATIONS

Fabris C., et al., "Are Risk Indices Derived From CGM Interchangeable With SMBG-Based Indices?," Journal of Diabetes Science and Technology, 2015 Diabetes Technology Society, vol. 10, No. 1, 2016, pp. 50-59.

International Search Report and Written Opinion for Application No. PCT/US2022/047873, mailed Jan. 18, 2023, 16 pages.

International Search Report and Written Opinion for Application No. PCT/US2022/047874 mailed Feb. 8, 2023, 11 pages.

International Search Report and Written Opinion for Application No. PCT/US2022/047876, mailed Feb. 8, 2023, 11 pages.

International Search Report and Written Opinion for Application No. PCT/US2022/047878, mailed Feb. 8, 2023, 11 pages.

International Search Report and Written Opinion for Application No. PCT/US2022/047880 mailed Feb. 10, 2023, 15 pages.

100

Person
102

104

124

Your Glucose

Your glucose is
increasing to the
highest level it has
been since this
morning.

Glucose Meas. 114

Computing Device 106

Glucose Monitoring
Application 116

Glucose Level
Deviation Detection
System 120

118

Glucose
Monitoring
Platform
110

Network
112

User Population
108

Glucose Meas. 114

Deviation Identification
Library 122

Glucose Level Deviation Detection System 120

Glucose Measurements 114

Data Collection Module 302

Collected Measurements 320

Metric Determination Module 304

Aggregate Metrics 322

Contextual Deviation Detection Module 308

Aggregate Metrics 322

Aggregate Metrics Store 324

Aggregate Metrics 322

Content-Based Deviation Detection Module 306

Deviation Indications 326

Deviation Indications 328

Deviation Selection Module 310

Deviation ID 330

Deviation Identification Library 122

Deviation ID 330

UI Module 312

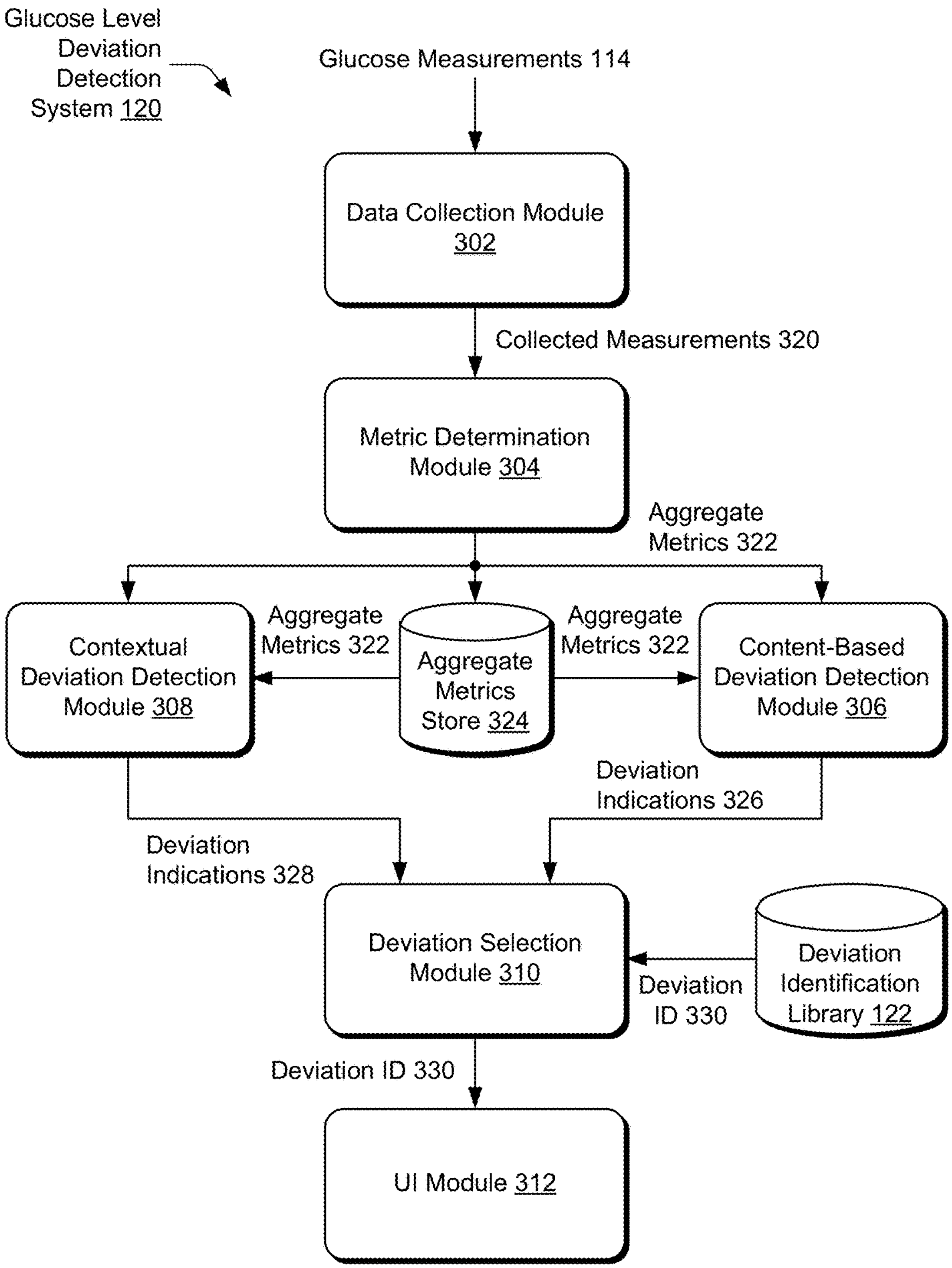

| | 12-1am | | 2:40-3:40pm | | 11pm-12am |
|---|---|---|---|---|---|
| Dec 27, 2021 | Risk Value | • • • | Risk Value | • • • | Risk Value |
| Dec 28, 2021 | Risk Value | • • • | Risk Value | • • • | Risk Value |
| Dec 29, 2021 | Risk Value | • • • | Risk Value | • • • | Risk Value |
| Dec 30, 2021 | Risk Value | • • • | Risk Value | • • • | Risk Value |
| Dec 31, 2021 | Risk Value | • • • | Risk Value | • • • | Risk Value |
| Jan 1, 2022 | Risk Value | • • • | Risk Value | | |

512

510

600

602
Obtain glucose measurements for a user for each of multiple time periods

604
Generate one or more aggregate metrics for the user during each of the multiple time periods

606
Determine whether an aggregate metric indicates a deviation from glucose measurements measured during a series of multiple preceding time periods

608
Generate a user interface identifying a deviation

610
Cause the user interface to be displayed

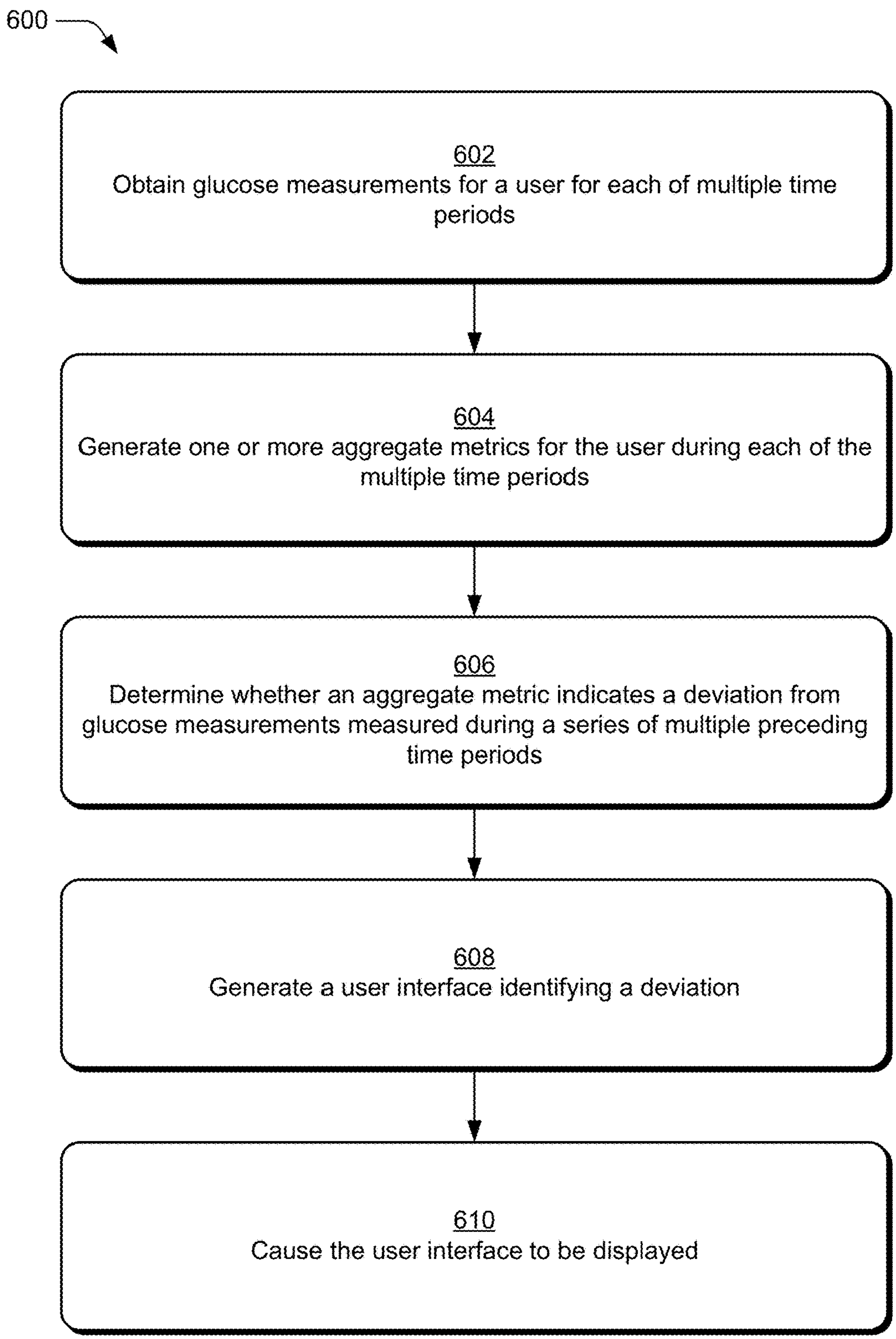

702
Obtain glucose measurements for a user for a time period of a current day

704
Generate one or more aggregate metrics for the user during the time period of the current day 706
Generate one or more aggregate metrics for the user during the corresponding time periods on each of multiple preceding days 708
Determine whether the one or more aggregate metrics for the time period of the current day indicate a deviation from glucose measurements measured during corresponding time periods on multiple preceding days 710
Generate a user interface identifying a deviation 712
Cause the user interface to be displayed

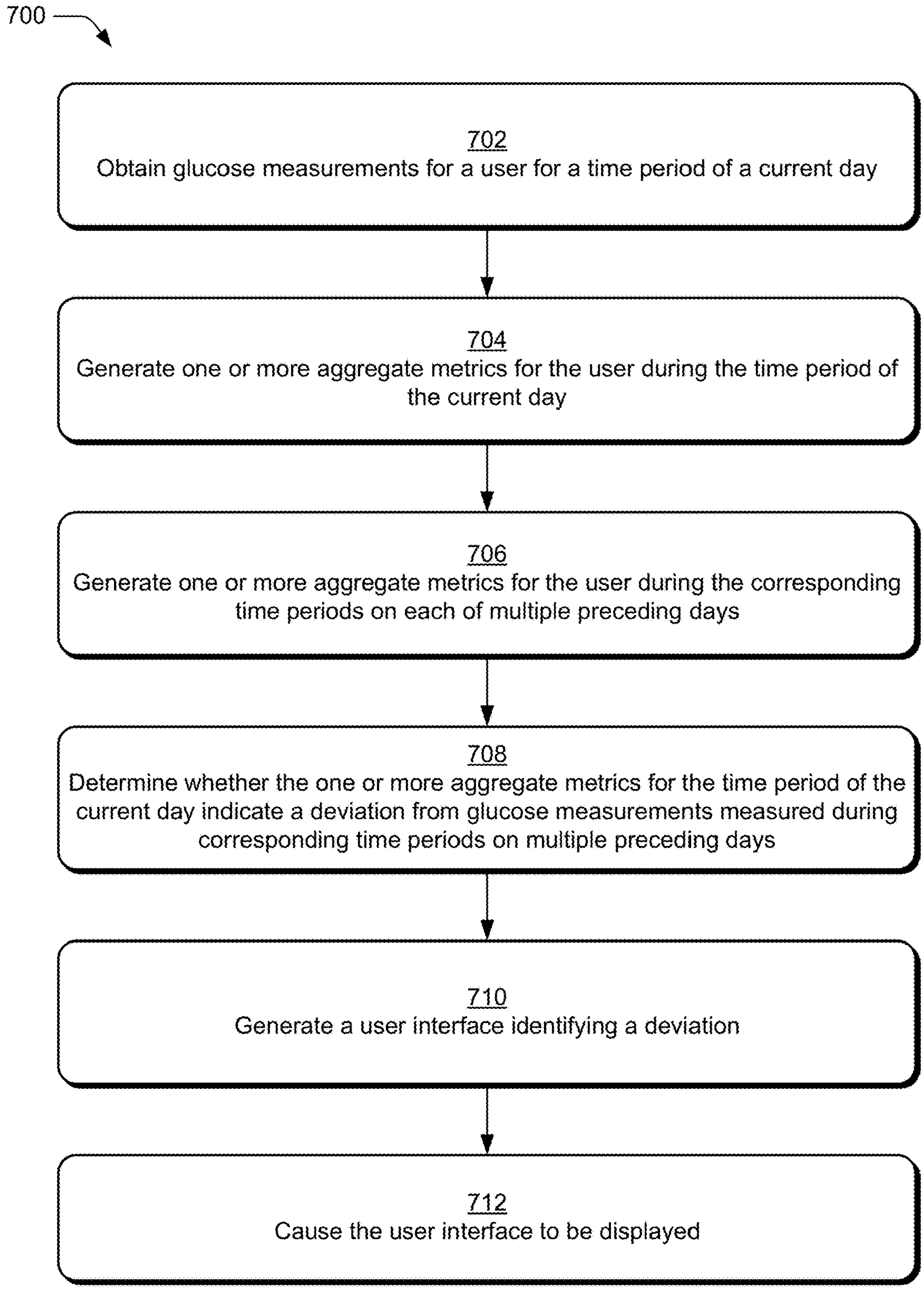

Platform 816

Resources 818

Glucose Monitoring
Platform 110

Cloud
814

Computing Device 802

Processing
System 804

Hardware
Elements 810

Computer-readable
Media 806

Memory/
Storage 812

I/O
Interfaces 808

Glucose Level
Deviation Detection
System 120

GLUCOSE LEVEL DEVIATION DETECTION

RELATED APPLICATIONS

This application claims the benefit of U.S. Provisional Patent Application No. 63/292,942, filed Dec. 22, 2021, and titled "Glucose Level Deviation Detection," the entire disclosure of which is hereby incorporated by reference, and also claims the benefit of U.S. Provisional Patent Application No. 63/263,188, filed Oct. 28, 2021, and titled "Ranking Feedback For Improving Diabetes Management," the entire disclosure of which is hereby incorporated by reference.

BACKGROUND

Diabetes is a metabolic condition affecting hundreds of millions of people and is one of the leading causes of death worldwide. For people living with Type I diabetes, access to treatment is critical to their survival and it can reduce adverse outcomes among people with Type II diabetes. With proper treatment, serious damage to the heart, blood vessels, eyes, kidneys, and nerves due to diabetes can be avoided. Regardless of the type of diabetes (e.g., Type I or Type II), managing diabetes successfully involves monitoring and oftentimes adjusting food and activity to control a person's blood glucose, such as to reduce severe fluctuations in and/or generally lower the person's glucose.

However, many conventional glucose monitoring applications employ user interfaces that display raw glucose information in a manner that is difficult for users to interpret, particularly users who have just recently started monitoring their glucose. Consequently, users may be unable to alter their behavior in a meaningful way in order to improve their glucose. Furthermore, over time these users often become overwhelmed and frustrated by the manner in which information is presented by these conventional glucose monitoring applications and thus discontinue use of these applications before improvements in their glucose and overall health can be realized. Moreover, as users increasingly utilize mobile devices (e.g., smart watches and smart phones) to access glucose monitoring information, the failure by conventional systems to provide meaningful glucose information in a manner that users can understand and act upon is further exacerbated by the constraints imposed by the small screens of these mobile devices.

SUMMARY

To overcome these problems, techniques for glucose level deviation detection are discussed. In one or more implementations, in a continuous glucose level monitoring system glucose measurements are obtained from a glucose sensor of the continuous glucose level monitoring system, the glucose sensor being inserted at an insertion site of the user. The glucose measurements are measured for a user for each of multiple time periods. A first aggregate metric for the user is generated during the time period. For a first time period of the multiple time periods, whether the first aggregate metric indicates a deviation by the first glucose measurements measured for the first time period from glucose measurements measured during a series of multiple time periods preceding the first time period is determined. In response to determining that the first aggregate metric indicates the deviation, a user interface identifying the deviation is generated (optionally only if the deviation is selected for display) and the user interface identifying the deviation is caused to be displayed.

In one or more implementations, in a continuous glucose level monitoring system glucose measurements are obtained from a glucose sensor of the continuous glucose level monitoring system, the glucose sensor being inserted at an insertion site of the user. The glucose measurements are measured for a user for a time period of a current day. An aggregate metric for the user during the time period of the current day is generated based on the glucose measurements for the time period. Further, based on glucose measurements for corresponding time periods on each of multiple preceding days, aggregate metrics for the user during the corresponding time periods on the multiple preceding days are generated. Whether the aggregate metric for the time period of the current day indicates a deviation by the glucose measurements measured for the time period of the current day from glucose measurements measured during the corresponding time periods on the multiple preceding days is determined. In response to determining that the aggregate metric for the time period of the current day indicates the deviation, a user interface identifying the deviation is generated (optionally only if the deviation is selected for display) and the user interface identifying the deviation is caused to be displayed.

This Summary introduces a selection of concepts in a simplified form that are further described below in the Detailed Description. As such, this Summary is not intended to identify essential features of the claimed subject matter, nor is it intended to be used as an aid in determining the scope of the claimed subject matter.

BRIEF DESCRIPTION OF THE DRAWINGS

The detailed description is described with reference to the accompanying figures.

FIG. 3 is an illustration of an example architecture of a glucose level deviation detection system.

FIG. 6 depicts a procedure in an example of implementing glucose level deviation detection.

FIG. 7 depicts a procedure in another example of implementing glucose level deviation detection.

DETAILED DESCRIPTION

Overview

Figure 1:
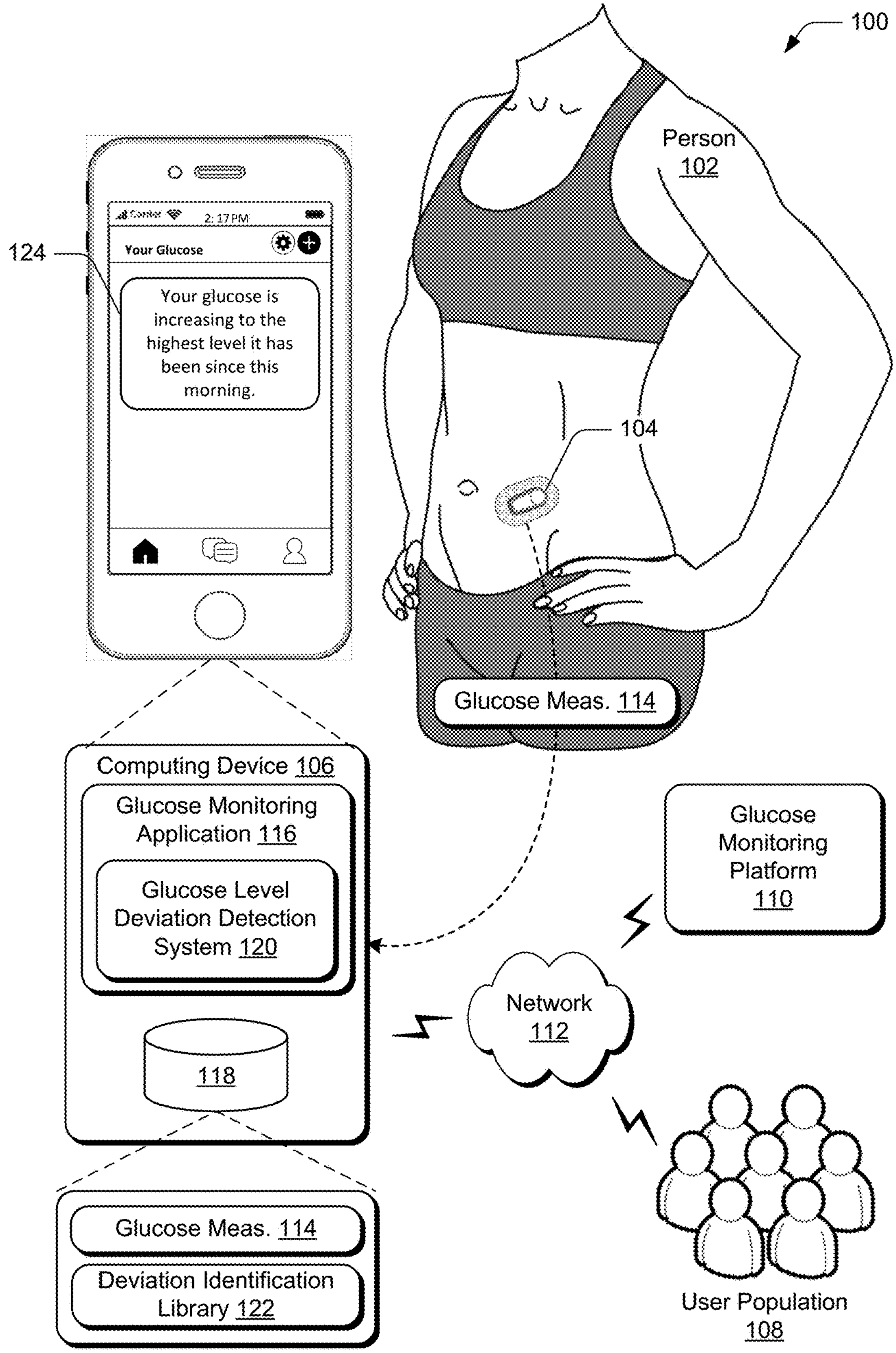
FIG. 1 is an illustration of an environment in an example of an implementation that is operable to implement glucose level deviation detection as described herein.

Techniques for glucose level deviation detection are discussed herein. Broadly, blood glucose level measurements of a user are obtained over time. These glucose level measurements can be obtained by a wearable glucose monitoring device being worn by the user. These glucose level measurements can be produced substantially continuously, such that the device may be configured to produce the glucose level measurements at regular or irregular intervals of time (e.g., approximately every hour, approximately every 30 minutes, approximately every 5 minutes, and so forth), responsive to establishing a communicative coupling with a different device (e.g., when a computing device establishes a wireless connection with a wearable glucose level monitoring device to retrieve one or more of the measurements), and so forth. These glucose level measurements are analyzed to detect deviations from past glucose measurements, such as glucose measurements received earlier in the day or glucose measurements received at corresponding times of one or more preceding days. Indications of detected deviations are provided to the user or communicated elsewhere, such as to a healthcare professional.

In one or more implementations, a data stream of glucose measurements is received. Aggregate metrics (e.g., hyperglycemic risk values, hypoglycemic risk values, mean glucose, mean coefficient of variation, etc.) are generated for collections of glucose measurements, such as over rolling windows of time (e.g., every 5 minutes, a collection of glucose measurements includes the glucose measurements during the preceding 30 or 60 minutes), at fixed 30-minute intervals (e.g., on every hour and every half hour of the day), the preceding 60 minutes, and so forth. These aggregate metrics are compared to aggregate metrics generated in other time periods to identify deviations in glucose measurements between time periods.

For example, risk values may be generated for time periods that include glucose measurements received between particular fixed times (e.g., approximately every half hour of the day). The aggregate metrics for a given time period are compared to the aggregate metrics over a number (e.g., 24) of immediately preceding time periods in the same day to determine whether the aggregate metrics for the given time period deviate from the aggregate metrics of the preceding time periods. If a deviation is detected, an indication that there is a deviation between the glucose measurements measured during the given time period and the glucose measurements measured during the preceding time periods is displayed or otherwise communicated. E.g., a user interface reading "Your glucose is increasing to the highest level it has been since this morning" may be displayed to the user.

By way of another example, aggregate metrics may be generated for time periods that include glucose measurements received over a preceding amount of time (e.g., every 5 minutes aggregate metrics are generated based on glucose measurements received over the preceding 60 minutes). The aggregate metrics for a given time period on the current day are compared to the aggregate metrics generated for the corresponding time periods on each of multiple preceding days to determine whether the aggregate metrics for the given time period deviate from the aggregate metrics of the corresponding time periods on the multiple preceding days. If a deviation is detected (and optionally if the deviation is selected for display), an indication that there is a deviation between the glucose measurements measured during the given time period on the current day and the glucose measurements measured during the preceding time periods is displayed or otherwise communicated. E.g., a user interface reading "Your glucose over the last hour is higher than it has been at this time for each of the past few days" may be displayed to the user.

The techniques discussed herein automatically detect deviations in glucose levels for the user and provide notifications of such to the user. This makes the user aware of the deviations in real time as they occur, alerting the user to the potential that they are doing something different that is having a significant impact on their glucose levels. This provides teachable moments to the user, helping the user make a connection between real time events or actions and changes in glucose levels, and thus alter their behavior now and in the future so as to avoid such changes in glucose levels (e.g., if the changes are bad) or to maintain such changes in glucose levels (e.g., if the changes are good). Furthermore, this allows warnings or updates to be communicated to healthcare providers so that those providers can help the user take correction action, be alerted to the severity of changes, and so forth.

In the following discussion, an example environment is first described that may employ the techniques described herein. Examples of implementation details and procedures are then described which may be performed in the example environment as well as other environments. Performance of the example procedures is not limited to the example environment and the example environment is not limited to performance of the example procedures.

Example of an Environment

FIG. 1 is an illustration of an environment 100 in an example of an implementation that is operable to implement glucose level deviation detection as described herein. The illustrated environment 100 includes a person 102, who is depicted wearing a wearable glucose monitoring device 104. The illustrated environment 100 also includes a computing device 106, other users in a user population 108 that wear glucose monitoring devices 104, and a glucose monitoring platform 110. The wearable glucose monitoring device 104, computing device 106, user population 108, and glucose monitoring platform 110 are communicatively coupled, including via a network 112.

Alternately or additionally, the wearable glucose monitoring device 104 and the computing device 106 may be communicatively coupled in other ways, such as using one or more wireless communication protocols or techniques. By way of example, the wearable glucose monitoring device 104 and the computing device 106 may communicate with one another using one or more of Bluetooth (e.g., Bluetooth Low Energy links), near-field communication (NFC), 5G, and so forth.

In accordance with the described techniques, the wearable glucose monitoring device 104 is configured to provide measurements of person 102's glucose. Although a wearable glucose monitoring device is discussed herein, it is to be appreciated that user interfaces for glucose monitoring may be generated and presented in connection with other devices capable of providing glucose measurements, e.g., non-wearable glucose devices such as blood glucose meters requiring finger sticks, patches, and so forth. In implementations that involve the wearable glucose monitoring device 104, though, it may be configured with a glucose sensor that continuously detects analytes indicative of the person 102's glucose and enables generation of glucose measurements. In the illustrated environment 100 and throughout the detailed description these measurements are represented as glucose measurements 114.

In one or more implementations, the wearable glucose monitoring device 104 is a continuous glucose monitoring ("CGM") system. As used herein, the term "continuous" used in connection with glucose monitoring may refer to an ability of a device to produce measurements substantially continuously, such that the device may be configured to produce the glucose measurements 114 at regular or irregular intervals of time (e.g., every hour, every 30 minutes, every 5 minutes, and so forth), responsive to establishing a communicative coupling with a different device (e.g., when a computing device establishes a wireless connection with the wearable glucose monitoring device 104 to retrieve one or more of the measurements), and so forth. This functionality along with further aspects of the wearable glucose monitoring device 104's configuration is discussed in more detail in relation to FIG. 2.

Additionally, the wearable glucose monitoring device 104 transmits the glucose measurements 114 to the computing device 106, such as via a wireless connection. The wearable glucose monitoring device 104 may communicate these measurements in real-time, e.g., as they are produced using a glucose sensor. Alternately or in addition, the wearable glucose monitoring device 104 may communicate the glucose measurements 114 to the computing device 106 at set time intervals. For example, the wearable glucose monitoring device 104 may be configured to communicate the glucose measurements 114 to the computing device 106 every five minutes (as they are being produced).

Certainly, an interval at which the glucose measurements 114 are communicated may be different from the examples above without departing from the spirit or scope of the described techniques. The measurements may be communicated by the wearable glucose monitoring device 104 to the computing device 106 according to other bases in accordance with the described techniques, such as based on a request from the computing device 106. Regardless, the computing device 106 may maintain the glucose measurements 114 of the person 102 at least temporarily, e.g., in computer-readable storage media of the computing device 106.

Although illustrated as a mobile device (e.g., a mobile phone), the computing device 106 may be configured in a variety of ways without departing from the spirit or scope of the described techniques. By way of example and not limitation, the computing device 106 may be configured as a different type of device, such as a mobile device (e.g., a wearable device, tablet device, or laptop computer), a stationary device (e.g., a desktop computer), an automotive computer, and so forth. In one or more implementations, the computing device 106 may be configured as a dedicated device associated with the glucose monitoring platform 110, e.g., with functionality to obtain the glucose measurements 114 from the wearable glucose monitoring device 104, perform various computations in relation to the glucose measurements 114, display information related to the glucose measurements 114 and the glucose monitoring platform 110, communicate the glucose measurements 114 to the glucose monitoring platform 110, and so forth.

Additionally, the computing device 106 may be representative of more than one device in accordance with the described techniques. In one or more scenarios, for instance, the computing device 106 may correspond to both a wearable device (e.g., a smart watch) and a mobile phone. In such scenarios, both of these devices may be capable of performing at least some of the same operations, such as to receive the glucose measurements 114 from the wearable glucose monitoring device 104, communicate them via the network 112 to the glucose monitoring platform 110, display information related to the glucose measurements 114, and so forth. Alternately or in addition, different devices may have different capabilities that other devices do not have or that are limited through computing instructions to specified devices.

In the scenario where the computing device 106 corresponds to a separate smart watch and a mobile phone, for instance, the smart watch may be configured with various sensors and functionality to measure a variety of physiological markers (e.g., heartrate, heartrate variability, breathing, rate of blood flow, and so on) and activities (e.g., steps or other exercise) of the person 102. In this scenario, the mobile phone may not be configured with these sensors and functionality, or it may include a limited amount of that functionality—although in other scenarios a mobile phone may be able to provide the same functionality. Continuing with this particular scenario, the mobile phone may have capabilities that the smart watch does not have, such as a camera to capture images associated with glucose monitoring and an amount of computing resources (e.g., battery and processing speed) that enables the mobile phone to more efficiently carry out computations in relation to the glucose measurements 114. Even in scenarios where a smart watch is capable of carrying out such computations, computing instructions may limit performance of those computations to the mobile phone so as not to burden both devices and to utilize available resources efficiently. To this extent, the computing device 106 may be configured in different ways and represent different numbers of devices than discussed herein without departing from the spirit and scope of the described techniques.

In accordance with the discussed techniques, the computing device 106 is configured to implement glucose level deviation detection. In the environment 100, the computing device 106 includes glucose monitoring application 116 and storage device 118. Here, the glucose monitoring application 116 includes the glucose level deviation detection system 120. Although illustrated as being included in computing device 106, additionally or alternatively at least some functionality of the glucose level deviation detection system 120 is located elsewhere, such as in glucose monitoring platform 110. Further, the glucose measurements 114 and deviation identification library 122 are shown stored in the storage device 118. The storage device 118 may represent one or more databases and also other types of storage capable of storing the glucose measurements 114 and the deviation identification library 122. The deviation identification library 122 stores multiple deviation identification items (e.g., messages or message templates) that can be provided to the user 102, for example to notify the user 102 in real time of current deviations in the user's glucose level relative to the user's glucose level earlier in the day or in corresponding times of previous days.

In one or more implementations, the glucose measurements 114 and/or the deviation identification library 122 may be stored at least partially remote from the computing device 106, e.g., in storage of the glucose monitoring platform 110, and retrieved or otherwise accessed in connection with configuring and outputting (e.g., displaying) user interfaces for deviation identification presentation. For instance, the glucose measurements 114 and/or the deviation identification library 122 may be generally stored in storage of the glucose monitoring platform 110 along with the glucose measurements of the user population 108 and/or the deviation identification library 122, and some of that data may be retrieved or otherwise accessed on an as-needed basis to display user interfaces for glucose level deviation identification presentation.

Broadly speaking, the glucose monitoring application 116 is configured to support interactions with a user that enable deviations in the user's glucose level to be identified and presented to the user 102. This may include, for example, obtaining the glucose measurements 114 for processing (e.g., to detect deviations), receiving information about a user (e.g., through an onboarding process and/or user feedback), causing information to be communicated to a health care provider, causing information to be communicated to the glucose monitoring platform 110, and so forth.

In one or more implementations, the glucose monitoring application 116 also leverages resources of the glucose monitoring platform 110 in connection with glucose level deviation detection. As noted above, for instance, the glucose monitoring platform 110 may be configured to store data, such as the glucose measurements 114 associated with a user (e.g., the person 102) and/or users of the user population 108, and the deviation identification library 122. The glucose monitoring platform 110 may also provide updates and/or additions to the glucose monitoring application 116. Further still, the glucose monitoring platform 110 may train, maintain, and/or deploy algorithms (e.g., machine learning algorithms) to detect deviations, select which of multiple deviations to present to the user 102, and so forth. One or more such algorithms may require an amount of computing resources that exceeds the resources of typical, personal computing devices, e.g., mobile phones, laptops, tablet devices, and wearables, to name just a few. Nonetheless, the glucose monitoring platform 110 may include or otherwise have access to the amount of resources needed to operate such algorithms, e.g., cloud storage, server devices, virtualized resources, and so forth. The glucose monitoring platform 110 may provide a variety of resources that the glucose monitoring application 116 leverages in connection with enabling deviations to be identified and presented via user interfaces.

In accordance with the described techniques, the glucose level deviation detection system 120 is configured to use the glucose measurements 114 to identify deviations in the glucose level of the user, to obtain one or more deviation identification items in the deviation identification library 122, and to cause output of one or more user interfaces that present the deviation identification items. The glucose monitoring application 116 may cause display of the configured user interface 124 via a display device of the computing device 106 or other display device.

As discussed above and below, a variety of glucose level deviation identifications (e.g., messages) may be selected or generated based on the glucose measurements 114 of the user in accordance with the described techniques. In the context of measuring glucose, e.g., continuously, and obtaining data describing such measurements, consider the following discussion of FIG. 2.

Figure 2:
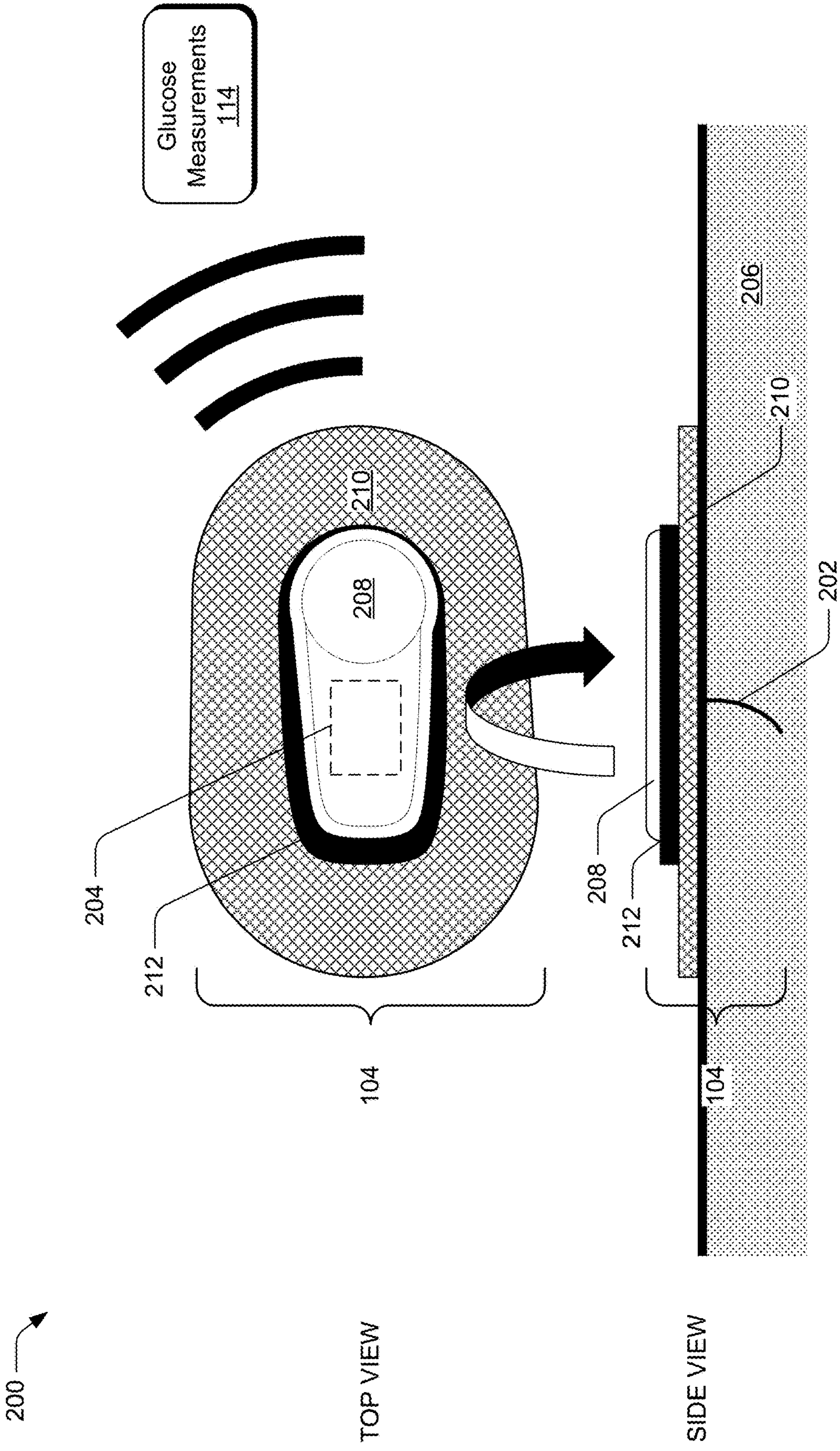
FIG. 2 depicts an example of an implementation of a wearable glucose monitoring device in greater detail.

FIG. 2 depicts an example 200 of an implementation of the wearable glucose monitoring device 104 of FIG. 1 in greater detail. In particular, the illustrated example 200 includes a top view and a corresponding side view of the wearable glucose monitoring device 104. It is to be appreciated that the wearable glucose monitoring device 104 may vary in implementation from the following discussion in various ways without departing from the spirit or scope of the described techniques. As noted above, for instance, user interfaces identifying detected deviations in glucose level may be configured and displayed (or otherwise output) in connection with other types of devices for glucose monitoring, such as non-wearable devices (e.g., blood glucose meters requiring finger sticks), patches, and so forth.

In this example 200, the wearable glucose monitoring device 104 is illustrated to include a sensor 202 and a sensor module 204. Here, the sensor 202 is depicted in the side view having been inserted subcutaneously into skin 206, e.g., of the person 102. The sensor module 204 is depicted in the top view as a dashed rectangle. The wearable glucose monitoring device 104 also includes a transmitter 208 in the illustrated example 200. Use of the dashed rectangle for the sensor module 204 indicates that it may be housed or otherwise implemented within a housing of the transmitter 208. In this example 200, the wearable glucose monitoring device 104 further includes adhesive pad 210 and attachment mechanism 212.

In operation, the sensor 202, the adhesive pad 210, and the attachment mechanism 212 may be assembled to form an application assembly, where the application assembly is configured to be applied to the skin 206 so that the sensor 202 is subcutaneously inserted as depicted. In such scenarios, the transmitter 208 may be attached to the assembly after application to the skin 206 via the attachment mechanism 212. Alternatively, the transmitter 208 may be incorporated as part of the application assembly, such that the sensor 202, the adhesive pad 210, the attachment mechanism 212, and the transmitter 208 (with the sensor module 204) can all be applied at once to the skin 206. In one or more implementations, this application assembly is applied to the skin 206 using a separate sensor applicator (not shown). Unlike the finger sticks required by conventional blood glucose meters, the user initiated application of the wearable glucose monitoring device 104 is nearly painless and does not require the withdrawal of blood. Moreover, the automatic sensor applicator generally enables the person 102 to embed the sensor 202 subcutaneously into the skin 206 without the assistance of a clinician or healthcare provider.

The application assembly may also be removed by peeling the adhesive pad 210 from the skin 206. It is to be appreciated that the wearable glucose monitoring device 104 and its various components as illustrated are simply one example form factor, and the wearable glucose monitoring device 104 and its components may have different form factors without departing from the spirit or scope of the described techniques.

In operation, the sensor 202 is communicatively coupled to the sensor module 204 via at least one communication channel which can be a wireless connection or a wired connection. Communications from the sensor 202 to the sensor module 204 or from the sensor module 204 to the sensor 202 can be implemented actively or passively and these communications can be continuous (e.g., analog) or discrete (e.g., digital).

The sensor 202 may be a device, a molecule, and/or a chemical which changes or causes a change in response to an event which is at least partially independent of the sensor 202. The sensor module 204 is implemented to receive indications of changes to the sensor 202 or caused by the sensor 202. For example, the sensor 202 can include glucose oxidase which reacts with glucose and oxygen to form hydrogen peroxide that is electrochemically detectable by the sensor module 204 which may include an electrode. In this example, the sensor 202 may be configured as or include a glucose sensor configured to detect analytes in blood or interstitial fluid that are indicative of glucose level using one or more measurement techniques. In one or more implementations, the sensor 202 may also be configured to detect analytes in the blood or the interstitial fluid that are indicative of other markers, such as lactate levels, which may improve accuracy in detecting various glucose level deviations. Additionally or alternately, the wearable glucose monitoring device 104 may include additional sensors to the sensor 202 to detect those analytes indicative of the other markers.

In another example, the sensor 202 (or an additional sensor of the wearable glucose monitoring device 104—not shown) can include a first and second electrical conductor and the sensor module 204 can electrically detect changes in electric potential across the first and second electrical conductor of the sensor 202. In this example, the sensor module 204 and the sensor 202 are configured as a thermocouple such that the changes in electric potential correspond to temperature changes. In some examples, the sensor module 204 and the sensor 202 are configured to detect a single analyte, e.g., glucose. In other examples, the sensor module 204 and the sensor 202 are configured to detect multiple analytes, e.g., sodium, potassium, carbon dioxide, and glucose. Alternately or additionally, the wearable glucose monitoring device 104 includes multiple sensors to detect not only one or more analytes (e.g., sodium, potassium, carbon dioxide, glucose, and insulin) but also one or more environmental conditions (e.g., temperature). Thus, the sensor module 204 and the sensor 202 (as well as any additional sensors) may detect the presence of one or more analytes, the absence of one or more analytes, and/or changes in one or more environmental conditions.

In one or more implementations, the sensor module 204 may include a processor and memory (not shown). The sensor module 204, by leveraging the processor, may generate the glucose measurements 114 based on the communications with the sensor 202 that are indicative of the above-discussed changes. Based on these communications from the sensor 202, the sensor module 204 is further configured to generate communicable packages of data that include at least one glucose measurement 114. In one or more implementations, the sensor module 204 may configure those packages to include additional data, including, by way of example and not limitation, a sensor identifier, a sensor status, temperatures that correspond to the glucose measurements 114, measurements of other analytes that correspond to the glucose measurements 114, and so forth. It is to be appreciated that such packets may include a variety of data in addition to at least one glucose measurement 114 without departing from the spirit or scope of the described techniques.

In implementations where the wearable glucose monitoring device 104 is configured for wireless transmission, the transmitter 208 may transmit the glucose measurements 114 wirelessly as a stream of data to a computing device. Alternately or additionally, the sensor module 204 may buffer the glucose measurements 114 (e.g., in memory of the sensor module 204 and/or other physical computer-readable storage media of the wearable glucose monitoring device 104) and cause the transmitter 208 to transmit the buffered glucose measurements 114 later at various intervals, e.g., time intervals (every second, every thirty seconds, every minute, every five minutes, every hour, and so on), storage intervals (when the buffered glucose measurements 114 reach a threshold amount of data or a number of measurements), and so forth.

Having considered an example of an environment and an example of a wearable glucose monitoring device, consider now a discussion of some examples of details of the techniques for glucose level deviation detection.

System Architecture

FIG. 3 is an illustration of an example architecture of a glucose level deviation detection system 120. The glucose level deviation detection system 120 includes a data collection module 302, a metric determination module 304, a content-based deviation detection module 306, a contextual deviation detection module 308, a deviation selection module 310, and a UI module 312. Generally, the glucose level deviation detection system 120 analyzes the glucose measurements 114 for the user 102 and looks for deviations from a norm for the user. These deviations from the norm can be based on various factors, such as metrics generated from the user's current or recent glucose level relative to metrics generated from the user's glucose levels earlier in the day, the metrics generated from the user's current or recent glucose level relative to metrics generated from the user's glucose levels in corresponding times of previous days, and so forth. Upon detection of one or more deviations, the glucose level deviation detection system 120 takes a responsive action, such as presenting an identification of the deviation to the user, communicating an identification of the deviation to a healthcare professional, and so forth.

More specifically, the data collection module 302 receives glucose measurements 114 for user 102. The glucose measurements 114 are received at a particular interval, such as approximately every 1 minute or approximately every 5 minutes. The glucose measurements 114 are grouped together into collections of measurements. In one or more implementations, the collections of measurements are set time periods within a 24-hour period, such as the glucose measurements 114 received during every half-hour time period (e.g., from 1:00 pm to 1:30 pm, from 1:30 pm to 2:00 pm, from 2:00 pm to 2:30 pm, and so forth). Additionally or alternatively, the collections of measurements are rolling windows of time, such as the glucose measurements 114 received over the previous 30 or 60 minutes. E.g., when a new glucose measurement 114 is received (such as approximately every 5 minutes), the data collection module 302 groups the glucose measurements 114 received over the previous 30 minutes or 1 hour into a collection of measurements. The data collection module 302 outputs the collections of measurements as collected measurements 320.

The metric determination module 304 receives the collected measurements 320 and generates one or more aggregate metrics 322 (or single-value metrics) from the collected measurements 320. An aggregate metric (also referred to as simply a metric) is a representation or summarization of the data in the collected measurements 320. The metric determination module 304 can generate any of a variety of different metrics based on the collected measurements 320. In one or more implementations, the metric determination module 304 generates risk values that are glycemic risk values indicating a potential health risk to the user 102 due to glucose levels.

Additionally or alternatively, the metric determination module 304 generates as aggregate metrics 322 any of a variety of statistics from the collected measurements 320, such as mean glucose measurement in the collected measurements 320, mean coefficient of variation for the glucose measurements in the collected measurements 320 (the ratio of the standard deviation to the mean for the glucose measurements in the collected measurements 320), mean amplitude of glycemic excursions (MAGE) for the glucose measurements in the collected measurements 320, the area under the glucose curve for the glucose measurements in the collected measurements 320, the area above the glucose curve for the glucose measurements in the collected measurements 320, the mean absolute rate of change for the glucose measurements in the collected measurements 320, the standard deviation of the glucose measurements in the collected measurements 320, the mean amount of time during which the collected measurements 320 were collected that the glucose measurements were below a particular glucose level (e.g., 250 mg/dL or 70 mg/dL), the mean amount of time during which the collected measurements 320 were collected that the glucose measurements were above a particular glucose level (e.g., 250 mg/dL), the maximum glucose measurement in the collected measurements 320, and so forth.

Additionally or alternatively the metric determination module 304 generates aggregate metrics 322 using different techniques for combining glucose measurements in the collected measurements 320, such as the median, the interquartile range (IQR), the XXth percentile, the standard deviation, and so forth.

Additionally or alternatively, the metric determination module 304 generates single-value metrics that are not an aggregate metric. For example, the metric determination module 304 can generate a metric that is a maximum glucose measurement in the collected measurements 320, an absolute rate of change for the glucose measurements in the collected measurements 320, and so forth. The metric determination module 304 outputs these single-value metrics which are used by the content-based deviation detection module 306 and the contextual deviation detection module 308 analogous to the aggregate metrics 322.

In one or more implementations, the aggregate metrics 322 are glycemic risk values indicating a potential health risk to the user 102 due to glucose levels. In one or more embodiments, these risk values include one or both of a hyperglycemic risk value and a hypoglycemic risk value. The hyperglycemic and hypoglycemic risk values can be determined in any of a variety of different manners.

In one or more embodiments, the hyperglycemic risk value is based on a high blood glucose index (HBGI) value generated for self-monitoring blood glucose (SMBG) readings. The HBGI value (HBGI) is generated by generating a risk r(BG) as $$r(BG)=10\cdot(1.509\cdot([\log(BG)]^{1.084}-5.381))^2$$

where BG refers to a collected measurement 320. The risk r(BG) balances the amplitude of hypoglycemic and hyperglycemic ranges (enlarging the amplitude of hypoglycemic ranges and shrinking the amplitude of hyperglycemic ranges) and makes the transformed data symmetric around zero and fitting a normal distribution.

The HBGI value (HBGI) is generated as $$HBGI = \frac{1}{N_h}\sum_{i=1}^{N_h} rh(BG_i)$$

where $N_h$ refers to a number of glucose measurements greater than a threshold level (e.g., 112.5 mg/dL) and $rh(BG_i)$ refers to the risk r(BG) values for each of the measurements greater than a threshold level (e.g., 112.5 mg/dL).

In one or more embodiments, the hypoglycemic risk value is based on a low blood glucose index (LBGI) value generated for SMBG readings. The LBGI value (LBGI) is generated as $$LBGI = \frac{1}{N_l}\sum_{i=1}^{N_l} rl(BG_i)$$

where $N_l$ refers to a number of glucose measurements less than a threshold level (e.g., 112.5 mg/dL) and $rl(BG_i)$ refers to the risk r(BG) values for each of the measurements less than a threshold level (e.g., 112.5 mg/dL).

The content-based deviation detection module 306 detects deviations from typical glucose level trends for the user in recent history by monitoring the aggregate metrics 322. This is also referred to as content-based deviation detection because the detection is performed based on recent glucose measurements. The content-based deviation detection module 306 receives the aggregate metrics 322 and determines, based on the aggregate metrics 322, whether the most recently collected measurements 320 indicate a deviation in glucose level for user 102 relative to previously collected measurements 320 (e.g., over the preceding 12 hours).

The content-based deviation detection module 306 determines whether there is a deviation in glucose level for user 102 at regular or irregular intervals based on a preceding time period. In one or more implementations, the metric determination module 304 generates aggregate metrics 322 approximately every 30 minutes, and the content-based deviation detection module 306 determines, in response to receiving new aggregate metrics 322 from metric determination module 304, whether there is a deviation in glucose level for user 102 approximately every 30 minutes by comparing the most recently received aggregate metrics 322 to the 24 previously received aggregate metrics 322 (e.g., the aggregate metrics 322 received over the previous 12 hours). Aggregate metrics 322 are stored, for example in an aggregate metrics store 324, so the previously received aggregate metrics 322 are readily available to the content-based deviation detection module 306. The aggregate metrics store 324 can be any of a variety of types of storage devices (e.g., random access memory, Flash memory, magnetic disk, and so forth).

Additionally or alternatively, other intervals or time periods can be used. For example, the metric determination module 304 may generate one or more aggregate metrics 322 approximately every 15 minutes, and the content-based deviation detection module 306 determines, in response to receiving a new aggregate metric 322 from metric determination module 304, whether there is a deviation in glucose level for user 102 approximately every 15 minutes by comparing the most recently received aggregate metric 322 to the aggregate metrics 322 received over the previous 10 hours. By way of another example, the metric determination module 304 may generate one or more aggregate metrics 322 approximately every 5 minutes (using a rolling window of the 30 previous minutes in time), and the content-based deviation detection module 306 determines, in response to receiving a new aggregate metric 322 from metric determination module 304, whether there is a deviation in glucose level for user 102 approximately every 5 minutes by comparing the most recently received aggregate metric 322 to the aggregate metrics 322 received over the previous 12 hours.

In one or more embodiments, the content-based deviation detection module 306 receives the most recently generated aggregate metrics 322 (e.g., the hypoglycemic risk value and hyperglycemic risk value most recently generated by the metric determination module 304) and generates predicted aggregate metrics (e.g., a predicted hypoglycemic risk value and a predicted hyperglycemic risk value) based on the previously received aggregate metrics 322. The content-based deviation detection module 306 compares the predicted aggregate metric to the received aggregate metric and determines that there is a deviation in glucose level for user 102 relative to previously collected measurements 320 if the predicted aggregate metric and the received aggregate metric differ by greater than a particular amount (e.g., greater than a threshold amount, such as 5.5). The content-based deviation detection module 306 outputs indications of deviations detected based on the aggregate metrics 322.

Figure 4:
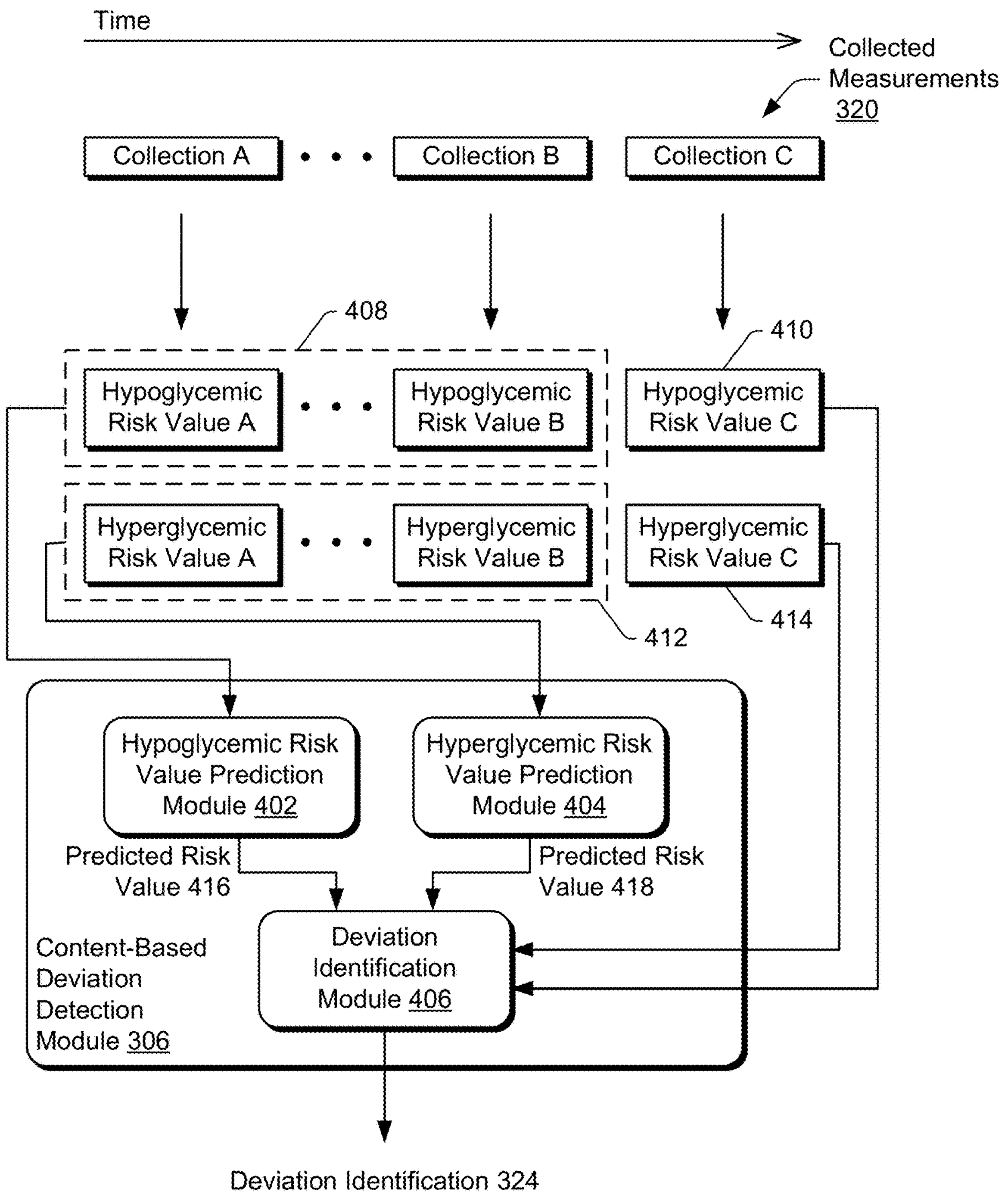
FIG. 4 is an illustration of an example implementation of the content-based deviation detection module.

FIG. 4 is an illustration of an example implementation of the content-based deviation detection module 306. In the example of FIG. 4 the aggregate metrics 322 include a hypoglycemic risk value and a hyperglycemic risk value. Although discussed with reference to hypoglycemic and hyperglycemic risk values, it should be noted that the content-based deviation detection module 306 can analogously use any other aggregate metrics in addition to, or in place of, the hypoglycemic and hyperglycemic risk values.

In the example of FIG. 4, the content-based deviation detection module 306 includes a hypoglycemic risk value prediction module 402, a hyperglycemic risk value prediction module 404, and a deviation identification module 406. Hypoglycemic risk values 408 and 410 and hyperglycemic risk values 412 and 414 are generated by the metric determination module 304 from collected measurements 320 as discussed above. As illustrated, a hypoglycemic risk value and a hyperglycemic risk value is generated for each collection of measurements 320. Hypoglycemic risk values 408 are provided to the hypoglycemic risk value prediction module 402. The hypoglycemic risk value prediction module 402 generates, based on the preceding hypoglycemic risk values 408, a predicted risk value 416 of the most recently received hypoglycemic risk value (actual hypoglycemic risk value 410 in the example of FIG. 4). Similarly, hyperglycemic risk values 412 are provided to the hyperglycemic risk value prediction module 404. The hyperglycemic risk value prediction module 404 generates, based on the preceding hyperglycemic risk values 412, a predicted risk value 418 of the most recently received hyperglycemic risk value (actual hyperglycemic risk value 414 in the example of FIG. 4).

In one or more implementations, the hypoglycemic risk prediction module 402 uses a machine learning system to generate the predicted risk value 416 and the hyperglycemic risk value prediction module 404 uses a machine learning system to generate the predicted risk value 418. Machine learning systems refer to a computer representation that can be tuned (e.g., trained) based on inputs to approximate unknown functions. In particular, machine learning systems can include a system that utilizes algorithms to learn from, and make predictions on, known data by analyzing the known data to learn to generate outputs that reflect patterns and attributes of the known data. For instance, a machine learning system can include decision trees, support vector machines, linear regression, logistic regression, Bayesian networks, random forest learning, dimensionality reduction algorithms, boosting algorithms, artificial neural networks, deep learning, and so forth.

The machine learning system of hypoglycemic risk value prediction module 402 is trained, for example, by using training data that is sets of multiple risk values. Each set of multiple (X) risk values includes a hypoglycemic risk value (values 1, . . . , X−1) for each of multiple collections of measurements. The machine learning system generates a predicted hypoglycemic risk value based on the training data value 1, . . . , X−1, and the machine learning system is trained by updating weights or values of layers in the machine learning system to minimize the loss between the predicted hypoglycemic risk value 416 and the actual hypoglycemic risk value (value X). Various different loss functions can be used in training the machine learning system, such as cross entropy loss, mean squared error loss, and so forth.

Similarly, the machine learning system of hyperglycemic risk value prediction module 404 is trained, for example, by using training data that is sets of multiple risk values. This training data can the same training data as is used to train the machine learning system of hypoglycemic risk value prediction module 402. Each set of multiple (X) risk values includes a hyperglycemic risk value (values 1, . . . , X−1) for each of multiple collections of measurements. The machine learning system generates a predicted hyperglycemic risk value based on the training data value 1, . . . , X−1, and the machine learning system is trained by updating weights or values of layers in the machine learning system to minimize the loss between the predicted hyperglycemic risk value 418 and the actual hyperglycemic risk value (value X). Various different loss functions can be used in training the machine learning system, such as cross entropy loss, mean squared error loss, and so forth.

In one or more embodiments, users are separated into different populations that have one or more similar characteristics. The user 102 is part of one of these different populations and the machine learning systems of the hypoglycemic risk value prediction module 402 and the hyperglycemic risk value prediction module 404 are trained using training data obtained from other users that are in the same population as the user 102 (e.g., and excluding any data obtained from users that are not in the same population as the user 102). The populations can be defined in any of a variety of different manners. In one or more embodiments, the populations are defined by diabetes diagnosis (e.g., the user does not have diabetes, the user has Type 1 diabetes, or the user has Type 2 non-insulin-dependent diabetes). Additionally or alternatively, the populations are defined in different manners, for example age-based populations. E.g., populations are based on whether the user is an adult or a child (e.g., older than 18 or younger than 18), based on an age bracket the user is in (e.g., 0-5 years old, 5-10 years old, 10-20 years old, 20-30 years old, etc.), and so forth. By way of another example, populations can be defined based on additional medical conditions a user may have, such as hypertension, obesity, cardiovascular disease, neuropathy, nephropathy, retinopathy, Alzheimer's, depression, and so forth. By way of another example, populations can be defined based on user habits or activities, such as exercise or other physical activities, sleep patterns, time spent working versus at leisure, and so forth. By way of another example, populations can be defined based on the manner in which glucose measurements 114 are obtained or the equipment used to obtain glucose measurements 114, such as whether glucose measurements 114 are obtained via CGM, a brand of wearable glucose monitoring device 104, a frequency with which glucose measurements 114 are obtained, and so forth.

By way of another example, populations can be defined based on past glucose measurements 114 for users, such as by grouping users by clustering based on past glucose measurements 114. Examples of such clusters include users with high glycemic variability, users with frequent hypoglycemia, users with frequent hyperglycemia, and so forth. By way of another example, users can be grouped by clustering by using the past activity data of the users (e.g., step counts, energy expenditure, exercise minutes, sleep hours, and so forth obtained from activity trackers worn by the users). Examples of such clusters include users with high average steps per day, users with low average energy expenditure per day, users with low average number of sleep hours, and so forth.

Separating users into different populations allows the glucose level deviation detection system 120 to be customized to the particular user 102, such as by training the machine learning system based on data from other users with similar characteristics. This improves the accuracy of the machine learning systems of the hypoglycemic risk value prediction module 402 and the hyperglycemic risk value prediction module 404 because data from users that differ from the particular user 102 need not be considered.

Although separate hypoglycemic risk value prediction module 402 and hyperglycemic risk value prediction module 404 are discussed, additionally or alternatively the content-based deviation detection module 306 includes a single risk value prediction module that generates both the predicted risk value 416 and the predicted risk value 418 (and optionally additional aggregate metrics). E.g., a single machine learning system may be trained to generate both the predicted risk value 416 and the predicted risk value 418 (and optionally other predicted aggregate metrics). Additionally or alternatively, the content-based deviation detection module 306 can include prediction modules to generate predicted aggregate metrics for other aggregate metrics (e.g., mean glucose, mean coefficient of variation, mean time in range, and so forth).

The deviation identification module 406 determines, based on the predicted risk value 416 and the actual risk value 410 whether there is a hypoglycemic deviation in glucose level for the user 102. The deviation identification module 406 can make this determination in any of a variety of different manners. In one or more embodiments, the deviation identification module 406 determines that there is a deviation in glucose level for the user 102 in response to the predicted risk value 416 and the actual risk value 410 differing by at least a threshold amount. This threshold amount can be a fixed value (e.g., 5.5) or a variable value (e.g. 10% of the predicted risk value 416 or of the actual risk value 410).

Similarly, the deviation identification module 406 determines, based on the predicted risk value 418 and the actual risk value 414 whether there is a hyperglycemic deviation in glucose level for the user 102. The deviation identification module 406 can make this determination in any of a variety of different manners. In one or more embodiments, the deviation identification module 406 determines that there is a deviation in glucose level for the user 102 in response to the predicted risk value 418 and the actual risk value 414 differing by at least a threshold amount. This threshold amount can be a fixed value (e.g., 5.5) or a variable value (e.g. 10% of the predicted risk value 418 or of the actual risk value 414).

The deviation identification module 406 outputs a deviation indication 326 indicating whether there is a deviation in glucose level (hyperglycemic or hypoglycemic) for user 102.

Thus, it can be seen that the deviation identification module 406 focuses on the error in the predictions by hypoglycemic risk value prediction module 402 and hyperglycemic risk value prediction module 404. A large prediction error indicates that the glucose measurements in the collected measurements 320 are changing in an unpredictable manner and thus are potentially deviating from the expected measurements.

Returning to FIG. 3, the contextual deviation detection module 308 detects real-time deviations from typical repeating glucose level trends found in the extended history of glucose levels for the user. This is also referred to as context-based outlier detection because the detection is performed based on current glucose levels in the context of the extended history of glucose levels for the user (e.g., the preceding 3 days, the preceding 2 weeks, etc.). The contextual deviation detection module 308 receives the aggregate metrics 322 and determines, based on the aggregate metrics 322, whether the most recently collected measurements 320 (e.g., received over the preceding hour) indicate a deviation in glucose level for user 102 relative to previously collected measurements 320 (e.g., over the corresponding time period in each of the preceding 3-14 days).

The contextual deviation detection module 308 determines whether there is a deviation in glucose level for user 102 based on a recent time period and the corresponding time period in each of multiple preceding days. The contextual deviation detection module 308 receives one or more aggregate metrics 322 from the metric determination module 304. Although illustrated as the same aggregate metrics, the content-based deviation detection module 306 and the contextual deviation detection module 308 optionally receive different aggregate metrics. For example, the content-based deviation detection module 306 and contextual deviation detection module 308 may receive aggregate metrics 322 at different time intervals, based on collected measurements 320 over different time periods or previous minutes of time, may receive aggregate metrics for different metrics (e.g., content-based deviation detection module 306 may receive hypoglycemic and hyperglycemic risk values whereas contextual deviation detection module 308 may receive mean glucose and mean amplitude of glycemic excursions metrics), and so forth.

In one or more implementations, the metric determination module 304 generates aggregate metrics 322 approximately every 5 minutes (using a rolling window of a particular time period, such as the 60 previous minutes in time) and the contextual deviation detection module 308 determines, in response to receiving a new aggregate metric 322 from metric determination module 304, whether there is a deviation in glucose level for user 102 approximately every 5 minutes by comparing the received aggregate metric 322 for the particular time period and the received aggregate metrics 322 for the corresponding time period in each of multiple preceding days. The data collection module 302 can generate a collection of measurements 320 and the metric determination module 304 can generate one or more aggregate metrics 322 in response to receipt of a glucose measurement 114.

The contextual deviation detection module 308 can compare the most recently generated aggregate metrics 322 (e.g., the hypoglycemic risk value and hyperglycemic risk value most recently generated by the metric determination module 304) to the aggregate metrics in the corresponding time period in each of multiple preceding days in any of a variety of different manners to determine whether there is a deviation in glucose level for the user 102.

In one or more embodiments, the contextual deviation detection module 308 generates a value representing or combining the aggregate metrics for the corresponding time period in each of multiple preceding days. For example, this value can be any of a variety of statistics, such as the average of the risk values in each of the multiple preceding days (or in subgroups of the multiple preceding days), the mean of the risk values in each of the multiple preceding days (or in subgroups of the multiple preceding days), and so forth. The contextual deviation detection module 308 determines that there is a deviation in glucose level for the user 102 in response to the difference between the value representing the aggregate metrics for the corresponding time period in each of multiple preceding days and the most recently generated aggregate metric 322 being at least a threshold amount. This threshold amount can be a fixed value (e.g., 7) or a variable value (e.g. 10% of the most recently received aggregate metric 322 or of the value representing the aggregate metrics for the corresponding time period in each of multiple preceding days).

The contextual deviation detection module 308 can use any of a variety of rules or criteria to determine the number of preceding days (or which preceding days) to compare the most recently generated aggregate metrics to. For example, the contextual deviation detection module 308 can compare the most recently generated aggregate metrics to the aggregate metrics for each preceding day over a pre-defined number of days, such as 14 days. The number of days can be pre-defined in various manners, such as by a developer or designer of the contextual deviation detection module 308, by user input from the user 102, by input from a healthcare provider, and so forth. By way of another example, the contextual deviation detection module 308 can compare the most recently generated aggregate metrics to the aggregate metrics for at least a particular number of days, then increasing the number (e.g., the aggregate metrics for the preceding 3 days, then the aggregate metrics for the preceding 4 days, then the aggregate metrics for the preceding 5 days, and so forth).

The contextual deviation detection module 308 determines whether there is a deviation in glucose level for the user 102 based on the aggregate metrics generated by the metric determination module 304. The contextual deviation detection module 308 outputs a deviation indication 328 indicating whether there is a deviation in glucose level (e.g., and an indication of the aggregate metric that resulted in the deviation in glucose level being identified) for user 102.

Figure 5:
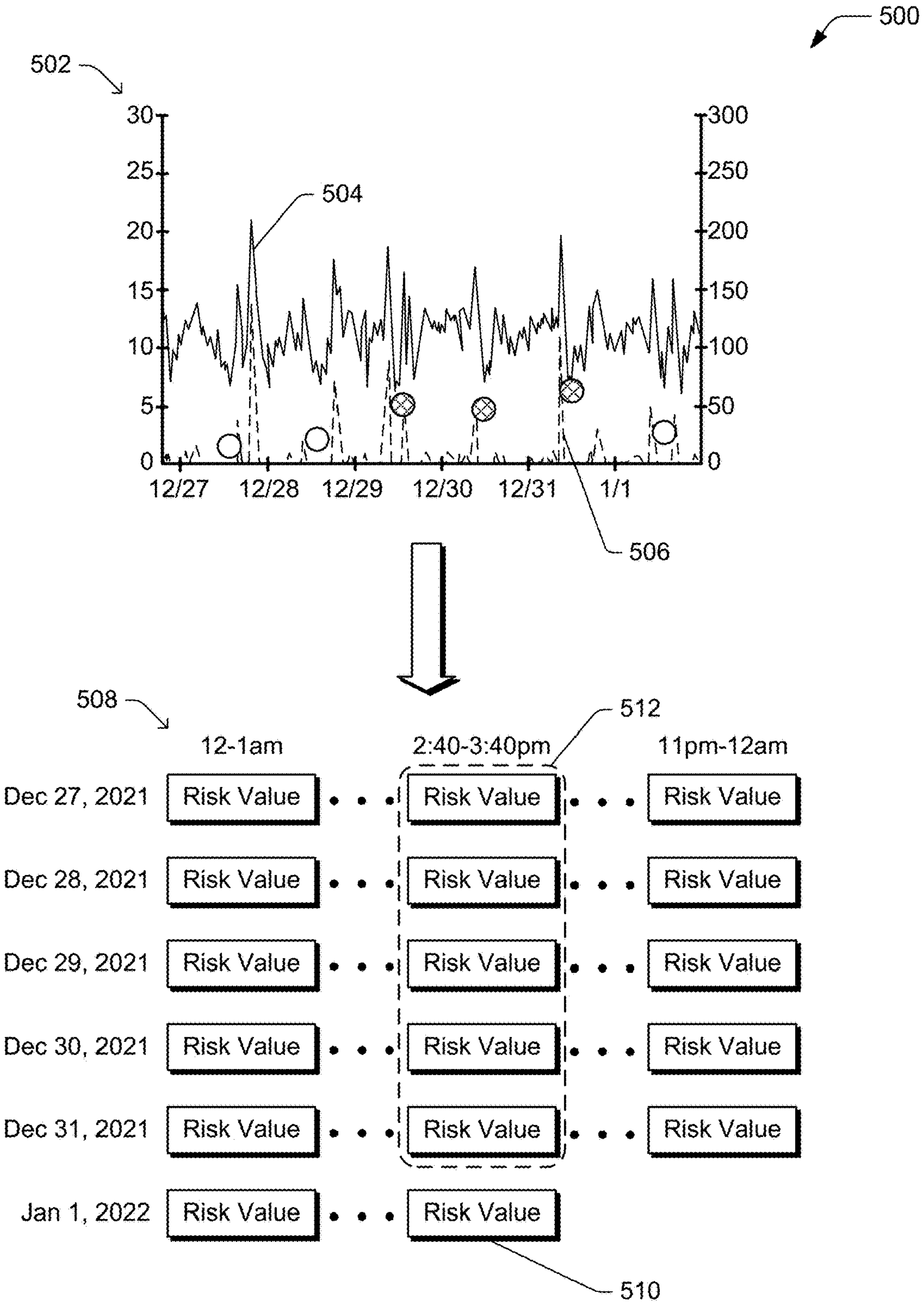
FIG. 5 illustrates an example of generating a deviation identification.

FIG. 5 illustrates an example 500 of generating a deviation indication 328. In the example of FIG. 5 the aggregate metrics 322 include hypoglycemic risk values. Although discussed with reference to hypoglycemic risk values, it should be noted that the contextual deviation detection module 308 can analogously use any other aggregate metrics in addition to, or in place of, the hypoglycemic risk values.

In the example of FIG. 5, the example 500 shows a graph 502 of glucose measurements and risk values over multiple days (December 27 through January 1). The graph 502 shows glucose measurements on the right ranging from 0 to 300 and hyperglycemic risk values on the left ranging from 0 to 30. A solid line 504 plots glucose measurements and a dashed line 506 plots hyperglycemic risk value precursors. Multiple risk values 508 are generated over 1-hour time periods.

In the illustrated example, the metric determination module 304 generates a hyperglycemic risk value 508 approximately every 5 minutes (using a rolling window of a 60-minute time period). The contextual deviation detection module 308 determines, in response to receiving a new hyperglycemic risk value 510 from metric determination module 304, whether there is a deviation in glucose level for user 102 for the preceding 60-minute period on the current day and the hyperglycemic risk values 512 for the corresponding time period in each of multiple preceding days. In the illustrated example, the contextual deviation detection module 308 receives the risk value 510 at approximately 3:40 pm on Jan. 1, 2022, and compares the risk value 510 to the risk values 512 corresponding to the same preceding 60 minutes (2:40-3:40 pm) from each of the days Dec. 27, 2021 through Dec. 31, 2021.

In the illustrated example, the contextual deviation detection module 308 determines that there is a deviation in glucose level for the user 102 in response to the difference between the most recently generated hyperglycemic risk value and the value representing the hyperglycemic risk value for the three immediately preceding days being at least a threshold amount. The hyperglycemic risk values for each day are illustrated by circles in the graph 502, with the hyperglycemic risk values for the three immediately preceding days being illustrated by circles with cross-hatched filling.

Returning to FIG. 3, the content-based deviation detection module 306 and the contextual deviation detection module 308 each allow glucose level deviations to be detected that the other module cannot detect. For example, glucose levels over a time period may be relatively consistent within a small range for the preceding 12 hours but be very different from the corresponding time periods in previous days. Thus, content-based deviation detection module 306 would not detect a deviation but contextual deviation detection module 308 would detect a deviation. By way of another example, glucose levels over a time period may be relatively consistent with the corresponding time periods in previous days but very different from the preceding 12 hours. Thus, contextual deviation detection module 308 would not detect a deviation but content-based deviation detection module 306 would detect a deviation.

The deviation selection module 310 receives the deviation indication 326 and the deviation indication 328 from the content-based deviation detection module 306 and the contextual deviation detection module 308, respectively. The deviation selection module 310 selects one or more of the deviation indication 326 and the deviation indication 328 and obtains a corresponding deviation identification 330 from the deviation identification library 122. The obtained deviation identification 330 is a message or communication that can be displayed or communicated to another device, user, healthcare professional, etc. that identifies or describes the corresponding deviation indication 326 or deviation indication 328. The deviation selection module 310 provides the obtained corresponding deviation identification 330 to UI module 312.

The deviation selection module 310 determines which deviation identification 330 corresponds to a deviation indication 326 or a deviation indication 328 in any of a variety of different manners. In one or more implementations, the deviation selection module 310 maintains a mapping of deviation identifications 330 to deviation indications. Additionally or alternatively, the deviation selection module 310 may use any of a variety of other rules or criteria to determine which deviation identification 330 corresponds to a deviation indication 326 or a deviation indication 328.

In one or more embodiments, the deviation selection module 310 selects a deviation identification 330 for each deviation identified in deviation indications 326 and deviation indications 328. This can result in deviation selection module 310 selecting multiple deviation identifications 330 that are displayed or otherwise presented by UI module 312.

Additionally or alternatively, in situations in which multiple deviation identifications are received, deviation selection module 310 selects a subset (e.g., one) of the deviations. The deviation selection module 310 can select one of the multiple deviations in various manners, such as randomly or pseudorandomly selecting one of the multiple deviations. Additionally or alternatively, the deviation selection module 310 can prioritize the multiple deviations and select one of the multiple deviations having a highest priority. For example, the deviation having the highest priority is selected.

The deviation selection module 310 optionally uses various criteria to determine which of the multiple deviations to select. These criteria can be based on various factors, such as how recently a deviation previously occurred, a ranking or prioritization of deviations or metrics, categories of deviations or metrics, how many consecutive days the deviations have occurred, and so forth. For example, a deviation that previously occurred less recently is selected over a deviation that occurred more recently. E.g., this allows different deviations to be selected and avoids repeatedly displaying the same deviation too frequently.

By way of another example, the deviation selection module 310 may select deviations from one of content-based deviation detection module 306 and contextual deviation detection module 308 over the other. E.g., the deviation selection module 310 may select a deviation identified by the content-based deviation detection module 306 over a deviation identified by the contextual deviation detection module 308. Or the deviation selection module 310 may select a deviation from the one of content-based deviation detection module 306 and contextual deviation detection module 308 that least recently identified a deviation.

By way of another example, a deviation designated (e.g., by a developer or designer of the deviation selection module 310) to be more urgent or safety-related is selected over a deviation that is less urgent or safety-related. E.g., this allows deviations corresponding to urgent or safety-related features (e.g., not staying within ranges or exceeding threshold glucose levels) to be selected over other non-urgent or non-safety-related features and display or otherwise present more critical diabetes management information to the user.

By way of another example, a deviation designated as being higher priority (e.g., by the user 102) may be selected over a deviation that is designated as being lower priority (e.g., by the user 102). E.g., this allows deviations that are of greater interest to the user to be displayed or otherwise presented rather than deviations that are of less interest to the user.

By way of another example, the deviation selection module 310 may select a deviation only if it has not been selected for at least a threshold amount of time. E.g., the deviation selection module 310 may select a deviation only if the deviation has not been selected for at least 30 minutes or for 2 days, the deviation selection module 310 may select a particular deviation only if at least a threshold number (e.g., 3 or 5) other deviations have been selected since that particular deviation was last selected, and so forth.

By way of another example, the deviation selection module 310 may select a deviation based on a population that the user 102 is a part of Populations can be defined or described in various manners as discussed above. As examples, certain deviations may be selected over other deviations based on whether the user is a Type 1 or Type 2 diabetic, based on how old the user is, based on other medical conditions the user has, and so forth.

By way of another example, the deviation selection module 310 may select a deviation based on other factors or input from various medical sources. As examples, certain deviations may be selected over other deviations based on input from subject matter experts (e.g., experts in the field of diabetes management), clinical guidelines, professional literature, and so forth.

The UI module 312 receives one or more deviation identifications 330 and causes the deviation identifications 330 to be displayed or otherwise presented (e.g., at computing device 106). This display or other presentation can take various forms, such as a static text display, graphic or video display, audio presentation, combinations thereof, and so forth. Additionally or alternatively, the one or more deviation identifications 330 can be communicated to or otherwise presented to a clinician, pharmacist, other health care provider, and so forth.

The particular content or message presented by the UI module 312 for a deviation identification 330 can vary. The content or message in the deviation identification 330 can be any appropriate text or other content based on the selected deviation. Examples of such content or messages include "Your glucose is a little higher than usual," "Your glucose is a little lower than usual," "Your glucose is a bit higher than it has been in the afternoon over the last few days," "Your glucose has risen quite a bit since this morning," "Your glucose is increasing to the highest level it has been since this morning," "Your glucose over the last hour is higher than it has been at this time for each of the past few days," and so forth.

Accordingly, the content or message in the deviation identification 330 can be a positive acknowledgement, such as a congratulatory acknowledgement of deviations trending away from normal behavior in a positive or self-serving way. Additionally or alternatively, the content or message in the deviation identification 330 can be a preemptive warning, such as acknowledging negatively trending deviations to preempt worsening patterns.

The UI module 312 can communicate, display, or otherwise present deviation identification 330 at any of a variety of different timings. In one or more embodiments, the UI module 312 communicates, displays, or otherwise presents deviation identification 330 in response to receiving the deviation identification 330 from deviation selection module 310 (e.g., at approximately the same time as the deviation is detected by content-based deviation detection module 306 or contextual deviation detection module 308). Additionally or alternatively, the UI module 312 communicates, displays, or otherwise presents deviation identification 330 at other times, such as at the completion of a meal, at regular or irregular intervals (e.g., approximately every 5 minutes, with the deviation selection module 310 optionally selecting a different one of multiple deviation identifications 330 every 5 minutes), in response to user input requesting a most recent deviation identification 330, and so forth.

The glucose level deviation detection system 120 optionally takes additional actions based on detected deviations (or the lack thereof). In one or more implementations, these actions include notifying the glucose monitoring application 116 or the wearable glucose monitoring device 104 that the frequency with which glucose measurements 114 are produced can be reduced or increased. For example, if the glucose level deviation detection system 120 identifies a time period for which no deviation is detected (e.g., for multiple days), the glucose level deviation detection system 120 notifies the glucose monitoring application 116 or wearable glucose monitoring device 104 that the frequency with which glucose measurements 114 are produced can be reduced (e.g., from every 5 minutes to every 10 minutes) during that time period, reducing the power expended to produce glucose measurements 114. By way of another example, if the glucose level deviation detection system 120 identifies a deviation for a time period, the glucose level deviation detection system 120 notifies the glucose monitoring application 116 or wearable glucose monitoring device 104 that the frequency with which glucose measurements 114 are produced can be increased (e.g., from every 5 minutes to every 2 minutes) during that time period on subsequent days or during subsequent time periods on the current day, increasing the accuracy of the generated risk values due to the increased number of glucose measurements 114.

Although discussed as using the aggregate metrics 322, additionally or alternatively the collected measurements 320 are provided to one or both of the content-based deviation detection module 306 and the contextual deviation detection module 308. In such situations, the content-based deviation detection module 306 or the contextual deviation detection module 308 identify deviations analogous to the discussion above but using the collected measurements 320 rather than the aggregate metrics 322.

Furthermore, glucose level deviation detection system 120 is discussed as including both content-based deviation detection module 306 and contextual deviation detection module 308, which can operate concurrently to generate deviation indications. Additionally or alternatively, the glucose level deviation detection system 120 includes only one of the content-based deviation detection module 306 and the contextual deviation detection module 308.

Having discussed exemplary details of the techniques for user interfaces for glucose insight presentation, consider now some examples of procedures to illustrate additional aspects of the techniques.

Example Procedures

This section describes examples of procedures for implementing glucose level deviation detection. Aspects of the procedures may be implemented in hardware, firmware, or software, or a combination thereof. The procedures are shown as a set of blocks that specify operations performed by one or more devices and are not necessarily limited to the orders shown for performing the operations by the respective blocks.

FIG. 6 depicts a procedure 600 in an example of implementing glucose level deviation detection. Procedure 600 is performed, for example, by a glucose level deviation detection system, such as the glucose level deviation detection system 120.

Glucose measurements for a user for each of multiple time periods are obtained (block 602). These glucose measurements are obtained from a glucose sensor of, for example, a continuous glucose level monitoring system with the glucose sensor being inserted at an insertion site of the user. These time periods are, for example, 30-minute periods of time.

One or more aggregate metrics are generated for the user during each of the multiple time periods (block 604). These one or more aggregate metrics can include, for example, hyperglycemic and hypoglycemic risk values (e.g., high blood glucose index and low blood glucose index), mean glucose, mean coefficient of variation, mean time in range, and so forth.

An aggregate metric indicates a deviation from glucose measurements measured during a series of multiple preceding time periods (block 606). For example, the determination is made as to whether the most recently generated aggregate metric indicates a deviation from glucose measurements measured during the preceding 12 hours.

A user interface identifying the deviation is generated (block 608). In some situations multiple deviations may be indicated in block 606, and in such situations one or more of the identified deviations is selected for inclusion in the user interface in block 608.

The user interface including the identified deviation is caused to be displayed (block 610) or otherwise presented. Additionally or alternatively, the identified or selected deviation can be communicated to or otherwise presented to a clinician, pharmacist, or other health care provider.

FIG. 7 depicts a procedure 700 in another example of implementing glucose level deviation detection. Procedure 700 is performed, for example, by a glucose level deviation detection system, such as the glucose level deviation detection system 120.

Glucose measurements for a user for a time period of a current day are obtained (block 702). These glucose measurements are obtained from a glucose sensor of, for example, a continuous glucose level monitoring system with the glucose sensor being inserted at an insertion site of the user. This time period is, for example, 30-minute periods of time.

One or more aggregate metrics are generated for the user during the time period of the current day (block 704). These one or more aggregate metrics can include, for example, hyperglycemic and hypoglycemic risk values (e.g., high blood glucose index and low blood glucose index), mean glucose, mean coefficient of variation, mean time in range, and so forth.

An aggregate metric is generated for the user during the corresponding time period on each of multiple preceding days (block 706). For example, these corresponding time periods are the same 30-minute periods of time as the time period of the current day. This aggregate metric is the same aggregate metric as at least one of the aggregate metrics generated in block 704. A determination is made as to whether the aggregate metric for the time period of the current day indicates a deviation from glucose measurements measured during corresponding time periods on the multiple preceding days (block 708).

A user interface identifying the deviation is generated (block 710). In some situations multiple deviations may be indicated in block 708, and in such situations one or more of the identified deviations is selected for inclusion in the user interface in block 710.

The user interface including the identified deviation is caused to be displayed (block 712) or otherwise presented. Additionally or alternatively, the identified or selected deviation can be communicated to or otherwise presented to a clinician, pharmacist, or other health care provider.

Example System and Device

Figure 8:
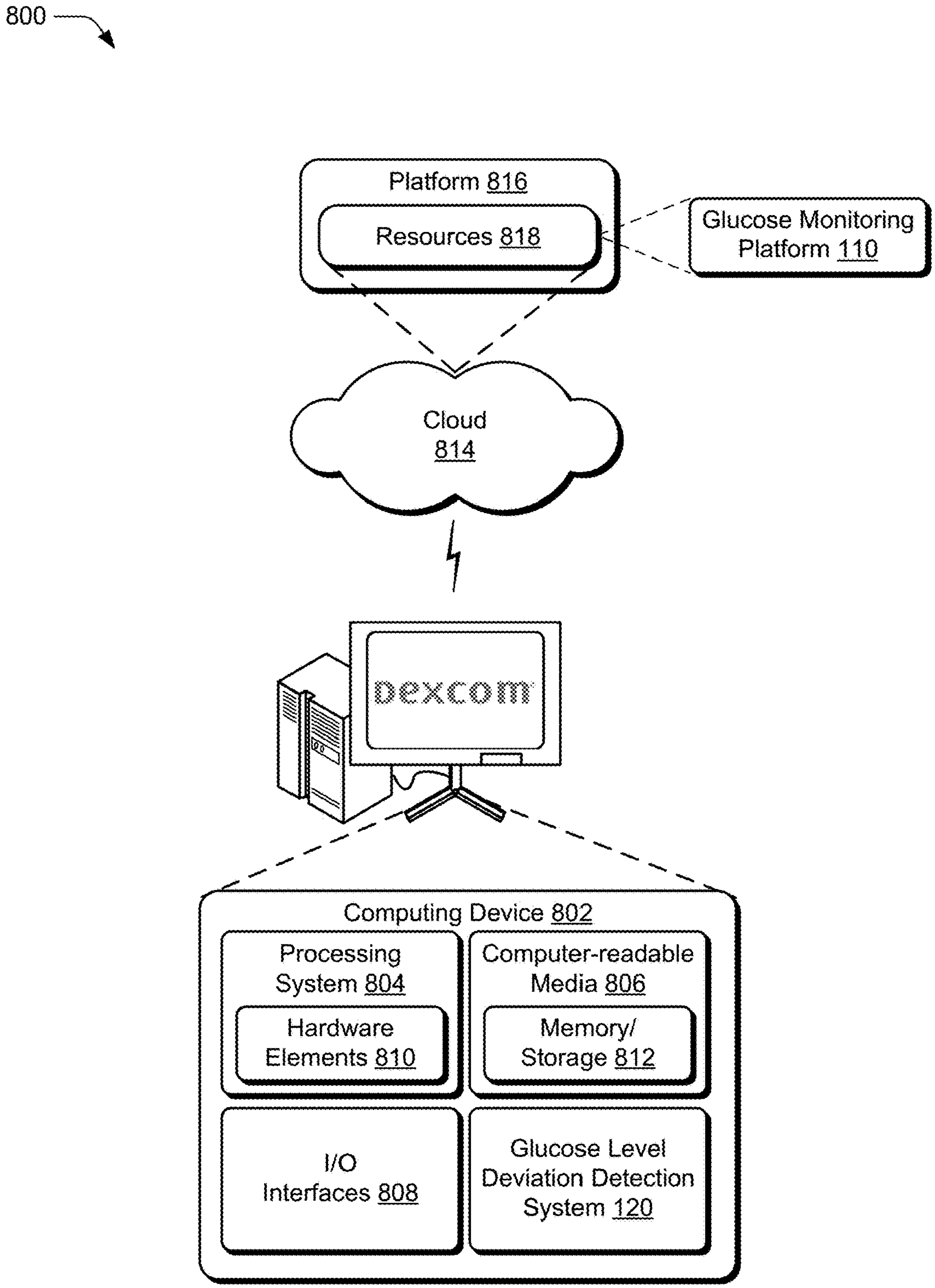
FIG. 8 illustrates an example of a system generally that includes an example of a computing device that is representative of one or more computing systems and/or devices that may implement the various techniques described herein.

FIG. 8 illustrates an example of a system generally at 800 that includes an example of a computing device 802 that is representative of one or more computing systems and/or devices that may implement the various techniques described herein. This is illustrated through inclusion of the glucose level deviation detection system 120. The computing device 802 may be, for example, a server of a service provider, a device associated with a client (e.g., a client device), an on-chip system, and/or any other suitable computing device or computing system.

The example computing device 802 as illustrated includes a processing system 804, one or more computer-readable media 806, and one or more I/O interfaces 808 that are communicatively coupled, one to another. Although not shown, the computing device 802 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 804 is representative of functionality to perform one or more operations using hardware. Accordingly, the processing system 804 is illustrated as including hardware elements 810 that may be configured as processors, functional blocks, and so forth. This may include implementation in hardware as an application specific integrated circuit or other logic device formed using one or more semiconductors. The hardware elements 810 are not limited by the materials from which they are formed, or the processing mechanisms employed therein. For example, processors may be comprised of semiconductor(s) and/or transistors (e.g., electronic integrated circuits (ICs)). In such a context, processor-executable instructions may be electronically-executable instructions.

The computer-readable media 806 is illustrated as including memory/storage component 812. The memory/storage component 812 represents memory/storage capacity associated with one or more computer-readable media. The memory/storage component 812 may include volatile media (such as random access memory (RAM)) and/or nonvolatile media (such as read only memory (ROM), Flash memory, optical disks, magnetic disks, and so forth). The memory/storage component 812 may include fixed media (e.g., RAM, ROM, a fixed hard drive, and so on) as well as removable media (e.g., Flash memory, a removable hard drive, an optical disc, and so forth). The computer-readable media 806 may be configured in a variety of other ways as further described below.

Input/output interface(s) 808 are representative of functionality to allow a user to enter commands and information to computing device 802, and also allow information to be presented to the user and/or other components or devices using various input/output devices. Examples of input devices include a keyboard, a cursor control device (e.g., a mouse), a microphone, a scanner, touch functionality (e.g., capacitive or other sensors that are configured to detect physical touch), a camera (e.g., which may employ visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 802 may be configured in a variety of ways as further described below to support user interaction.

Various techniques may be described herein in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. The features of the techniques described herein are platform-independent, meaning that the techniques may be implemented on a variety of commercial computing platforms having a variety of processors.

An implementation of the described modules and techniques may be stored on or transmitted across some form of computer-readable media. The computer-readable media may include a variety of media that may be accessed by the computing device 802. By way of example, computer-readable media may include "computer-readable storage media" and "computer-readable signal media."

"Computer-readable storage media" may refer to media and/or devices that enable persistent and/or non-transitory storage of information thereon in contrast to mere signal transmission, carrier waves, or signals per se. Thus, computer-readable storage media refers to non-signal bearing media. The computer-readable storage media includes hardware such as volatile and non-volatile, removable and non-removable media and/or storage devices implemented in a method or technology suitable for storage of information such as computer readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable signal media" may refer to a signal-bearing medium that is configured to transmit instructions to the hardware of the computing device 802, such as via a network. Signal media typically may embody computer readable instructions, data structures, program modules, or other data in a modulated data signal, such as carrier waves, data signals, or other transport mechanism. Signal media also include any information delivery media. The term "modulated data signal" means a signal that has one or more of its characteristics set or changed in such a manner as to encode information in the signal. By way of example, communication media include wired media such as a wired network or direct-wired connection, and wireless media such as acoustic, RF, infrared, and other wireless media.

As previously described, hardware elements 810 and computer-readable media 806 are representative of modules, programmable device logic and/or fixed device logic implemented in a hardware form that may be employed in some embodiments to implement at least some aspects of the techniques described herein, such as to perform one or more instructions. Hardware may include components of an integrated circuit or on-chip system, an application-specific integrated circuit (ASIC), a field-programmable gate array (FPGA), a complex programmable logic device (CPLD), and other implementations in silicon or other hardware. In this context, hardware may operate as a processing device that performs program tasks defined by instructions and/or logic embodied by the hardware as well as a hardware utilized to store instructions for execution, e.g., the computer-readable storage media described previously.

Combinations of the foregoing may also be employed to implement various techniques described herein. Accordingly, software, hardware, or executable modules may be implemented as one or more instructions and/or logic embodied on some form of computer-readable storage media and/or by one or more hardware elements 810. The computing device 802 may be configured to implement particular instructions and/or functions corresponding to the software and/or hardware modules. Accordingly, implementation of a module that is executable by the computing device 802 as software may be achieved at least partially in hardware, e.g., through use of computer-readable storage media and/or hardware elements 810 of the processing system 804. The instructions and/or functions may be executable/operable by one or more articles of manufacture (for example, one or more computing devices 802 and/or processing systems 804) to implement techniques, modules, and examples described herein.

The techniques described herein may be supported by various configurations of the computing device 802 and are not limited to the specific examples of the techniques described herein. This functionality may also be implemented all or in part through use of a distributed system, such as over a "cloud" 814 via a platform 816 as described below.

The cloud 814 includes and/or is representative of a platform 816 for resources 818. The platform 816 abstracts underlying functionality of hardware (e.g., servers) and software resources of the cloud 814. The resources 818 may include applications and/or data that can be utilized while computer processing is executed on servers that are remote from the computing device 802. Resources 818 can also include services provided over the Internet and/or through a subscriber network, such as a cellular or Wi-Fi network.

The platform 816 may abstract resources and functions to connect the computing device 802 with other computing devices. The platform 816 may also serve to abstract scaling of resources to provide a corresponding level of scale to encountered demand for the resources 818 that are implemented via the platform 816. Accordingly, in an interconnected device embodiment, implementation of functionality described herein may be distributed throughout the system 800. For example, the functionality may be implemented in part on the computing device 802 as well as via the platform 816 that abstracts the functionality of the cloud 814.

In some aspects, the techniques described herein relate to a method implemented in a continuous glucose level monitoring system, the method including: obtaining, from a glucose sensor of the continuous glucose level monitoring system for each of multiple time periods, glucose measurements measured for a user for the time period, the glucose sensor being inserted at an insertion site of the user; generating, based on the glucose measurements for each of the multiple time periods, a first aggregate metric for the user during the time period; determining, for a first time period of the multiple time periods, whether the first aggregate metric indicates a deviation by the first glucose measurements measured for the first time period from glucose measurements measured during a series of multiple time periods preceding the first time period; generating, in response to determining that the first aggregate metric indicates the deviation, a user interface identifying the deviation; and causing the user interface identifying the deviation to be displayed.

In some aspects, the techniques described herein relate to a method, wherein the determining includes: predicting, based on the aggregate metrics for the series of multiple time periods preceding the first time period, an aggregate metric for the first time period; determining a difference between the predicted aggregate metric for the first time period and the first aggregate metric; and determining that the first aggregate metric indicates a deviation in response to the difference exceeding a threshold amount.

In some aspects, the techniques described herein relate to a method, further including: generating, based on the glucose measurements for each of the multiple time periods, aggregate metrics for the user during the time period; determining, for the first time period of the multiple time periods, whether the aggregate metrics for the first time period indicate an additional deviation by the first glucose measurements measured for the first time period from glucose measurements measured during a series of multiple time periods preceding the first time period; generating, in response to determining that the aggregate metrics for the first time period indicate the additional deviation, a user interface identifying the additional deviation; and causing the user interface identifying the additional deviation to be displayed.

In some aspects, the techniques described herein relate to a method, wherein the aggregate metrics includes high blood glucose index values.

In some aspects, the techniques described herein relate to a method, wherein the aggregate metrics includes low blood glucose index values.

In some aspects, the techniques described herein relate to a method, wherein the determining includes determining whether the aggregate metrics for the first time period indicate a deviation using a machine learning system trained with sets of multiple aggregate metrics as training data and trained to minimize a loss between a predicted aggregate metric and an actual aggregate metric.

In some aspects, the techniques described herein relate to a method, wherein each of the multiple time periods includes 30 minutes and the multiple time periods include 24 time periods.

In some aspects, the techniques described herein relate to a method, further including: obtaining, from the glucose sensor for a time period of a current day, glucose measurements measured for the user for the time period; generating, based on the glucose measurements for the time period, a second aggregate metric for the user during the time period of the current day; generating, based on glucose measurements for corresponding time periods on each of multiple preceding days, aggregate metrics for the user during the corresponding time periods on the multiple preceding days; determining whether the second aggregate metric indicates a deviation by the first glucose measurements measured for the first time period of the current day from glucose measurements measured during the corresponding time periods on the multiple preceding days; generating, in response to determining that the second aggregate metric indicates the deviation, a user interface identifying the deviation; and causing the user interface identifying the deviation to be displayed.

In some aspects, the techniques described herein relate to a method, wherein the deviation is one of multiple deviations, and the method further including: identifying a population of which the user is a part; and selecting one of the multiple deviations based on the population, the population being one of multiple different populations of users, and the generating including generating the user interface identifying the selected deviation.

In some aspects, the techniques described herein relate to a method, wherein the identifying the population of which the user is a part includes identifying the population of which the user is a part based on an age of the user or a diabetes diagnosis of the user.

In some aspects, the techniques described herein relate to a computing device including: a processor; a display device; and computer-readable storage media having stored thereon multiple instructions of an application that, responsive to execution by the processor, cause the processor to: obtain, from a glucose sensor of a continuous glucose level monitoring system for each of multiple time periods, glucose measurements measured for a user for the time period, the glucose sensor being inserted at an insertion site of the user; generate, based on the glucose measurements for each of the multiple time periods, an aggregate metric for the user during the time period; determine, for a first time period of the multiple time periods, whether the aggregate metric for the first time period indicates a deviation by the first glucose measurements measured for the first time period from glucose measurements measured during a series of multiple time periods preceding the first time period; generate, in response to determining that the aggregate metric for the first time period indicates the deviation, a user interface identifying the deviation; and cause the user interface identifying the deviation to be displayed on the display device.

In some aspects, the techniques described herein relate to a computing device, wherein the deviation is one of multiple deviations, and the multiple instructions further cause the processor to: identify a population of which the user is a part; and select one of the multiple deviations based on the population, the population being one of multiple different populations of users, and wherein to generate the user interface is to generate the user interface identifying the selected deviation.

In some aspects, the techniques described herein relate to a computing device, wherein the multiple instructions further cause the processor to: generate, based on the glucose measurements for each of the multiple time periods, aggregate metrics for the user during the time period; determine, for the first time period of the multiple time periods, whether the aggregate metrics for the first time period indicate an additional deviation by the first glucose measurements measured for the first time period from glucose measurements measured during the series of multiple time periods preceding the first time period; generate, in response to determining that the aggregate metrics for the first time period indicate the additional deviation, a user interface identifying the additional deviation; and cause the user interface identifying the additional deviation to be displayed on the display device.

In some aspects, the techniques described herein relate to a computing device, wherein the aggregate metric includes high blood glucose index values.

In some aspects, the techniques described herein relate to a computing device, wherein the aggregate metric includes low blood glucose index values.

In some aspects, the techniques described herein relate to a computing device, wherein to determine whether the aggregate metric for the first time period indicates a deviation is to determine whether the aggregate metrics for the first time period indicate a deviation using a machine learning system trained with sets of multiple aggregate metrics as training data and trained to minimize a loss between a predicted risk aggregate metric an actual aggregate metric.

In some aspects, the techniques described herein relate to a computing device, wherein the user is part of one population of multiple different populations of users, and the using a machine learning system includes using a machine learning system trained with training data for the one population.

In some aspects, the techniques described herein relate to a method implemented in a continuous glucose level monitoring system, the method including: obtaining, from a glucose sensor of the continuous glucose level monitoring system for a time period of a current day, glucose measurements measured for a user for the time period, the glucose sensor being inserted at an insertion site of the user; generating, based on the glucose measurements for the time period, an aggregate metric for the user during the time period of the current day; generating, based on glucose measurements for corresponding time periods on each of multiple preceding days, aggregate metrics for the user during the corresponding time periods on the multiple preceding days; determining whether the aggregate metric for the time period of the current day indicates a deviation by the glucose measurements measured for the time period of the current day from glucose measurements measured during the corresponding time periods on the multiple preceding days; generating, in response to determining that the aggregate metric for the time period of the current day indicates the deviation, a user interface identifying the deviation; and causing the user interface identifying the deviation to be displayed.

In some aspects, the techniques described herein relate to a method, further including: generating a value representing the aggregate metrics for the user during the corresponding time periods on the multiple preceding days, and wherein the determining includes determining that the aggregate metric for the time period of the current day indicates a deviation by the glucose measurements measured for the time period of the current day from glucose measurements measured during the corresponding time periods on the multiple preceding days in response to a difference between the value representing the aggregate metrics for the user during the corresponding time periods on the multiple preceding days and the aggregate metric for the user during the time period of the current day exceeding a threshold amount.

In some aspects, the techniques described herein relate to a method, wherein the value representing the aggregate metrics for the user during the corresponding time periods on the multiple preceding days includes a mean or average of the aggregate metrics for the user during the corresponding time periods on the multiple preceding days.

In some aspects, the techniques described herein relate to a method, wherein the deviation is one of multiple deviations, and the method further including: identifying a population of which the user is a part and selecting one of the multiple deviations based on the population, wherein the population is one of multiple different populations of users, and the generating the user interface includes generating the user interface identifying the selected deviation.

In some aspects, the techniques described herein relate to a method, wherein the identifying the population of which the user is a part includes identifying the population of which the user is a part based on an age of the user or a diabetes diagnosis of the user.

In some aspects, the techniques described herein relate to a device including a continuous glucose level monitoring system, the device including: a display device; a data collection module, implemented at least in part in hardware, to obtain, from a glucose sensor for a time period of a current day, glucose measurements measured for a user for the time period, the glucose sensor being inserted at an insertion site of the user; a deviation detection module, implemented at least in part in hardware, to generate, based on the glucose measurements for the time period, an aggregate metric for the user during the time period of the current day, and to generate, based on glucose measurements for corresponding time periods on each of multiple preceding days, aggregate metrics for the user during the corresponding time periods on the multiple preceding days; and a deviation selection module, implemented at least in part in hardware, to determine whether the aggregate metric for the time period of the current day indicates a deviation by the glucose measurements measured for the time period of the current day from glucose measurements measured during the corresponding time periods on the multiple preceding days, to generate, in response to determining that the aggregate metric for the time period of the current day indicates the deviation, a user interface identifying the deviation, and to cause the user interface identifying the deviation to be displayed.

In some aspects, the techniques described herein relate to a device, further including a metric determination module, implemented at least in part in hardware, to generate a value representing the aggregate metrics for the user during the corresponding time periods on the multiple preceding days, and wherein the deviation selection module is further to determine that the aggregate metric for the time period of the current day indicates a deviation by the glucose measurements measured for the time period of the current day from glucose measurements measured during the corresponding time periods on the multiple preceding days in response to a difference between the value representing the aggregate metrics for the user during the corresponding time periods on the multiple preceding days and the aggregate metric for the user during the time period of the current day exceeding a threshold amount.

In some aspects, the techniques described herein relate to a device, wherein the value representing the aggregate metrics for the user during the corresponding time periods on the multiple preceding days includes a mean or average of the aggregate metrics for the user during the corresponding time periods on the multiple preceding days.

Conclusion

Although the systems and techniques have been described in language specific to structural features and/or methodological acts, it is to be understood that the systems and techniques defined in the appended claims are not necessarily limited to the specific features or acts described. Rather, the specific features and acts are disclosed as example forms of implementing the claimed subject matter.

What is claimed is:

1. A method implemented in a continuous glucose level monitoring system, the method comprising:

obtaining, from a glucose sensor of the continuous glucose level monitoring system for each of multiple time periods, glucose measurements measured for a user for the time period, the glucose sensor being inserted at an insertion site of the user;

generating, based on the glucose measurements for each of the multiple time periods, a plurality of aggregate metrics for the user during the time period;

measuring, from the plurality of aggregate metrics, a first aggregate metric for the user during a first time period;

predicting, for the first time period, a predicted aggregate metric for the user based on the plurality of aggregate metrics generated for a series of multiple time periods preceding the first time period;

determining an error as an absolute difference between the predicted aggregate metric and the first aggregate metric for the first time period;

determining that a deviation is present when the error exceeds a pre-determined threshold;

generating, in response to determining that the error exceeds the pre-determined threshold, a user interface identifying the deviation; and causing the user interface identifying the deviation to be displayed.

2. The method of claim 1, further comprising:

determining, for the first time period of the multiple time periods, whether the plurality of aggregate metrics for the first time period indicate an additional deviation by first glucose measurements measured for the first time period from glucose measurements measured during the series of multiple time periods preceding the first time period;

generating, in response to determining that the plurality of aggregate metrics for the first time period indicate the additional deviation, a user interface identifying the additional deviation; and causing the user interface identifying the additional deviation to be displayed.

3. The method of claim 1, wherein the plurality of aggregate metrics includes high blood glucose index values.

4. The method of claim 1, wherein the plurality of aggregate metrics includes low blood glucose index values.

5. The method of claim 1, wherein the determining includes determining whether the plurality of aggregate metrics for the first time period indicate the deviation using a machine learning system trained with sets of multiple aggregate metrics as training data and trained to minimize a loss between the predicted aggregate metric and an actual aggregate metric.

6. The method of claim 1, wherein each of the multiple time periods comprises 30 minutes and the multiple time periods include 24 time periods.

7. The method of claim 1, further comprising:

obtaining, from the glucose sensor for a time period of a current day, glucose measurements measured for the user for the time period;

generating, based on the glucose measurements for the time period, a second aggregate metric for the user during the time period of the current day;

generating, based on glucose measurements for corresponding time periods on each of multiple preceding days, aggregate metrics for the user during the corresponding time periods on the multiple preceding days;

determining whether the second aggregate metric indicates an additional deviation by first glucose measurements measured for the first time period of the current day from glucose measurements measured during the corresponding time periods on the multiple preceding days;

generating, in response to determining that the second aggregate metric indicates the additional deviation, a user interface identifying the additional deviation; and causing the user interface identifying the additional deviation to be displayed.

8. The method of claim 1, wherein the deviation is one of multiple deviations, and the method further comprising:

identifying a population of which the user is a part; and selecting one of the multiple deviations based on the population, the population being one of multiple different populations of users, and the generating comprising generating the user interface identifying the selected deviation.

9. The method of claim 8, wherein the identifying the population of which the user is a part comprises identifying the population of which the user is a part based on an age of the user or a diabetes diagnosis of the user.

10. A computing device comprising:

a processor;

a display device; and computer-readable storage media having stored thereon multiple instructions of an application that, responsive to execution by the processor, cause the processor to:

obtain, from a glucose sensor of a continuous glucose level monitoring system for each of multiple time periods, glucose measurements measured for a user for the time period, the glucose sensor being inserted at an insertion site of the user;

generate, based on the glucose measurements for each of the multiple time periods, plurality of aggregate metrics for the user during the time period;

measure, from the plurality of aggregate metrics, a first aggregate metric for the user during a first time period;

predict, for the first time period, a predicted aggregate metric for the user based on the plurality of aggregate metrics generated for a series of multiple time periods preceding the first time period;

determine an error as an absolute difference between the predicted aggregate metric and the first aggregate metric for the first time period;

determine that a deviation is present when the error exceeds a pre-determined threshold;

generate, in response to determining that the error exceeds the pre-determined threshold, a user interface identifying the deviation; and cause the user interface identifying the deviation to be displayed on the display device.

11. The computing device of claim 10, wherein the deviation is one of multiple deviations, and the multiple instructions further cause the processor to:

identify a population of which the user is a part; and select one of the multiple deviations based on the population, the population being one of multiple different populations of users, and wherein to generate the user interface is to generate the user interface identifying the selected deviation.

12. The computing device of claim 10, wherein the multiple instructions further cause the processor to:

determine, for the first time period of the multiple time periods, whether the plurality of aggregate metrics for the first time period indicate an additional deviation by first glucose measurements measured for the first time period from glucose measurements measured during the series of multiple time periods preceding the first time period;

generate, in response to determining that the plurality of aggregate metrics for the first time period indicate the additional deviation, a user interface identifying the additional deviation; and cause the user interface identifying the additional deviation to be displayed on the display device.

13. The computing device of claim 10, wherein to determine whether the first aggregate metric for the first time period indicates the deviation is to determine whether the plurality of aggregate metrics for the first time period indicate the deviation using a machine learning system trained with sets of multiple aggregate metrics as training data and trained to minimize a loss between a predicted risk aggregate metric and an actual aggregate metric.

14. The computing device of claim 13, wherein the user is part of one population of multiple different populations of users, and the using a machine learning system includes using a machine learning system trained with training data for the one population.

15. A method implemented in a continuous glucose level monitoring system, the method comprising:

obtaining, from a glucose sensor of the continuous glucose level monitoring system for a time period of a current day, glucose measurements measured for a user for the time period, the glucose sensor being inserted at an insertion site of the user;

generating, based on the glucose measurements for the time period, an aggregate metric for the user during the time period of the current day;

generating, based on glucose measurements for corresponding time periods on each of multiple preceding days, a plurality of aggregate metrics for the user during the corresponding time periods on the multiple preceding days;

predicting, for the time period of the current day, a predicted aggregate metric for the user based on the plurality of aggregate metrics generated for the user during the corresponding time periods on the multiple preceding days;

determining an error as an absolute difference between the predicted aggregate metric and the aggregate metric for the user during the time period of the current day;

determining that a deviation is present when the error exceeds a pre-determined threshold;

generating, in response to determining that the error exceeds the pre-determined threshold, a user interface identifying the deviation; and causing the user interface identifying the deviation to be displayed.

16. The method of claim 15, further comprising:

generating a value representing the plurality of aggregate metrics for the user during the corresponding time periods on the multiple preceding days, and wherein the determining comprises determining that the aggregate metric for the time period of the current day indicates an additional deviation by the glucose measurements measured for the time period of the current day from glucose measurements measured during the corresponding time periods on the multiple preceding days in response to a difference between the value representing the plurality of aggregate metrics for the user during the corresponding time periods on the multiple preceding days and the aggregate metric for the user during the time period of the current day exceeding a threshold amount.

17. The method of claim 16, wherein the value representing the plurality of aggregate metrics for the user during the corresponding time periods on the multiple preceding days includes a mean or average of the plurality of aggregate metrics for the user during the corresponding time periods on the multiple preceding days.

18. The method of claim 15, wherein the deviation is one of multiple deviations, and the method further comprising:

identifying a population of which the user is a part; and selecting one of the multiple deviations based on the population, wherein the population is one of multiple different populations of users, and the generating the user interface comprises generating the user interface identifying the selected deviation.

19. The method of claim 18, wherein the identifying the population of which the user is a part comprises identifying the population of which the user is a part based on an age of the user or a diabetes diagnosis of the user.

* * * * *